United States Patent [19]

Meki et al.

[11] Patent Number: 5,028,714

[45] Date of Patent: Jul. 2, 1991

[54] HYDROXYLAMINE ETHERS

[75] Inventors: Naoto Meki, Kobe; Kazue Nishida, Tokyo; Tomotoshi Imahase, Takarazuka; Hiroaki Fujimoto, Toyonaka; Kenichi Mikitani, Takarazuka; Hirotaka Takano, Sanda; Yoriko Ogasawara, Toyonaka; Masahiro Tamaki, Takarazuka, all of Japan

[73] Assignee: Sumitomo Chemical Company, Limited, Osaka, Japan

[21] Appl. No.: 596,375

[22] Filed: Oct. 12, 1990

Related U.S. Application Data

[62] Division of Ser. No. 410,425, Sep. 21, 1989, Pat. No. 4,980,345.

[30] Foreign Application Priority Data

Jan. 27, 1989 [JP] Japan ................................. 01-018215
Apr. 28, 1989 [JP] Japan ................................. 01-110661
Sep. 29, 1989 [JP] Japan ................................. 63-248677

[51] Int. Cl.$^5$ ........................................... C07D 239/20
[52] U.S. Cl. ................................. 546/300; 546/338; 564/300; 564/301
[58] Field of Search ............... 546/300, 308; 564/300, 564/301

[56] References Cited

U.S. PATENT DOCUMENTS 4,751,245  6/1988  Bisacchi et al. ................. 564/300

OTHER PUBLICATIONS

EPA 0,341,048, (11-1989).

Primary Examiner—Robert W. Ramsuer
Attorney, Agent, or Firm—Stevens, Davis, Miller & Mosher

[57] ABSTRACT

There are disclosed a pyrazole compound represented by the formula

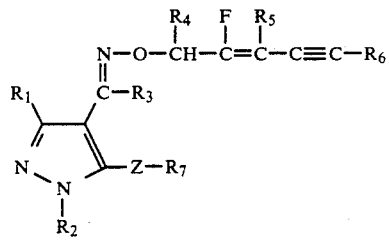

wherein the substituents of $R_1$ to $R_7$ and the symbol Z have the specified meanings as described in the text, an insecticidal, acaricidal and fungicidal composition containing the same, use of said composition for control of insects, acarids and fungi and a method of preparing said compound, and its intermediate.

1 Claim, No Drawings

HYDROXYLAMINE ETHERS

This is a division of application Ser. No. 07/410,425, filed Sept. 21, 1989, now U.S. Pat. No. 4,980,345

The present invention relates to a novel pyrazole compound, a method for its production, an insecticidal, acaricidal and fungicidal composition containing it as an active ingredient and intermediates for producing it.

It is disclosed in EP 234,045-A2 and JP-A-64-13086 that certain pyrazole compounds have insecticidal, acaricidal and fungicidal activity.

These compounds, however, may not always be said to be satisfactory in terms of the efficiency efficacy and spectrum of their activities.

In view of such situation, the present inventors have extensively studied to develop a compound having excellent activity, and as a result, have found that the pyrazole compound represented by the following formula (I) has particularly excellent insecticidal, acaricidal, and fungicidal activity. The present inventors thus have completed the present invention.

The present invention provides a pyrazole compound represented by the formula (I) [hereinafter referred to as present compound(s)], a method for its production, an insecticidal, acaricidal, and fungicidal composition containing it as an active ingredient and intermediates for producing it:

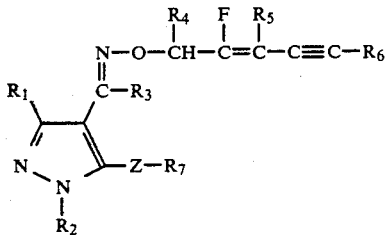

wherein $R_1$ is a hydrogen atom, or an alkyl or phenyl group; $R_2$ is a hydrogen atom, or an alkyl or haloalkyl group; $R_3$ is a hydrogen atom, or an alkyl or phenyl group; each of $R_4$ and $R_5$, which may be the same or different, is a hydrogen atom or an alkyl group; $R_6$ is a hydrogen atom, or an alkyl, haloalkyl, alkenyl, alkoxyalkyl, alkylthioalkyl, trialkylsilyl or dialkylphenyl silyl group, or an optionally substituted cycloalkyl, cycloalkenyl, phenyl or pyridyl group; $R_7$ is an alkyl, haloalkyl, alkenyl, haloalkenyl, alkynyl, haloalkynyl, alkoxyalkyl, alkylthioalkyl or mono or dialkylaminoalkyl group, or an optionally substituted cycloalkyl or cycloalkenyl group, or a group represented by

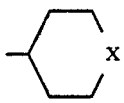

(in which X is an oxygen or sulfur atom), or a group represented by

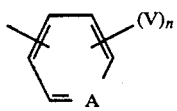

(in which each of V's, which may be the same or different, is a hydrogen or halogen atom, or an alkyl, haloalkyl, alkoxyl, haloalkoxyl or methylenedioxy group, A is a nitrogen atom or a methine group, and n is an integer of from 1 to 5); and Z is an oxygen or sulfur atom.

Where the present compound represented by the formula (I) contains one or more asymmetric carbon atoms, the compound may be an optical isomer in (+)-form, (−)-form or mixture thereof, and further, where the compound includes geometric isomers in its structure, it may be a cis-form, trans-form or mixture thereof.

The formula (I) representing the present compounds will be explained below.

In the definitions of $R_1$, the alkyl group is preferably a $C_1$–$C_4$ alkyl group. In the definitions of $R_2$, the alkyl and haloalkyl groups are preferably a $C_1$–$C_4$ alkyl group and may be substituted with chlorine, bromine or fluorine, respectively. In the definitions of $R_3$, the alkyl group is preferably a $C_1$–$C_2$ alkyl group. In the definitions of $R_4$ and $R_5$, the alkyl group is preferably a $C_1$–$C_3$ alkyl group. In the definitions of $R_6$, the alkyl, haloalkyl, alkenyl, alkoxyalkyl, alkylthioalkyl, cycloalkyl, and cycloalkenyl groups are preferably a $C_1$–$C_8$ alkyl group, a $C_1$–$C_8$ alkyl group substituted with a chlorine, bromine or fluorine atom, a $C_2$–$C_8$ alkenyl group, a $C_2$–$C_8$ alkoxyalkyl group, a $C_2$–$C_8$ alkylthioalkyl group, a $C_3$–$C_8$ cycloalkyl group and a $C_3$–$C_8$ cycloalkenyl group, respectively, and the substituents substituted on the cycloalkyl, cycloalkenyl, phenyl and pyridyl groups include a $C_1$–$C_3$ alkyl group, a $C_1$–$C_3$ alkoxy group and a halogen atom (e.g. chlorine, bromine, fluorine). The alkyl moieties of the trialkylsilyl or dialkylphenylsilyl group include a $C_1$–$C_2$ alkyl group. In the definitions of $R_7$, the alkyl, alkenyl and alkynyl groups are preferably those having 1(2) to 8 carbon atoms; the haloalkyl, haloalkenyl and haloalkynyl groups are preferably those having 1(2) to 8 carbon atoms substituted with a chlorine, bromine or fluorine atom; the alkoxyalkyl, alkylthioalkyl and mono or dialkylaminoalkyl groups are preferably those having 2 to 10 carbon atoms; the cycloalkyl and cycloalkenyl groups are preferably a $C_3$–$C_8$ cycloalkyl and cycloalkenyl groups, respectively; and the substituents subsituted on the cycloalkyl and cycloalkenyl groups include a $C_1$–$C_3$ alkyl group, a $C_1$–$C_3$ alkoxy group and a halogen atom (e.g. chlorine, bromine, fluorine). In the definitions of V, the halogen atom is preferably a chlorine, bromine or fluorine atom; the alkyl group is preferably a $C_1$–$C_4$ alkyl group; the haloalkyl group is preferably a $C_1$–$C_2$ alkyl group substituted with a chlorine, bromine or fluorine atom; the alkoxyl group is preferably a $C_1$–$C_4$ alkoxyl group; and the haloalkoxyl group is preferably a $C_1$–$C_4$ alkoxyl group substituted with a chlorine, bromine or fluorine atom.

Preferred compounds of the present invention, include those represented by the formula (I) in which $R_1$ is a hydrogen atom or an alkyl group, $R_2$ is a methyl group, and $R_3$ is a hydrogen atom. More preferred ones, include those represented by the formula (I) in which all of $R_4$, $R_5$ and $R_6$ are hydrogen atoms and $R_1$, $R_2$ and $R_3$ have the same meanings as mentioned above. As illustrative examples, the following compounds may be nominated:

1,3-Dimethyl-5-phenoxypyrazol-4-carboaldoxime O-2-fluoro-6,6-dimethylhept-2-ene-4-ynyl ether;

1,3-Dimethyl-5-(p-fluorophenoxy)pyrazol-4-carboaldoxime O-2-fluoro-6,6-dimethyl-6-methoxyhex-2-ene-4-ynyl ether;
1,3-Dimethyl-5-(3,5-difluorophenoxy)pyrazol-4-carboaldoxime O-2-fluoro-6,6-dimethyl-6-methoxyhex-2-ene-4-ynyl ether;
1,3-Dimethyl-5-phenoxypyrazol-4-carboaldoxime O-2-fluoro-5-trimethylsilylpent-2-ene-4-ynyl ether;
1,3-Dimethyl-5-phenoxypyrazol-4-carboaldoxime O-2-fluoro-5-(dimethylphenylsilyl)pent-2-ene-4-ynyl ether;
1,3-Dimethyl-5-phenoxypyrazol-4-carboaldoxime O-2-fluoro-6,6-dimethyloct-2-ene-4-ynyl ether;
1,3-Dimethyl-5-phenoxypyrazol-4-carboaldoxime O-2-fluoro-6-methylhept-2-ene-4-ynyl ether;
1,3-Dimethyl-5-phenoxypyrazol-4-carboaldoxime O-2-fluoro-5-cyclohexylpent-2-ene-4-ynyl ether;
1,3-Dimethyl-5-phenoxypyrazol-4-carboaldoxime O-2-fluoropent-2-ene-4-ynyl ether;
1,3-Dimethyl-5-phenoxypyrazol-4-carboaldoxime O-2-fluoro-5-phenylpent-2-ene-4-ynyl ether;
1,3-Dimethyl-5-isopropyloxypyrazol-4-carboaldoxime O-2-fluoro-6,6-dimethylhept-2-ene-4-ynyl ether;
1,3-Dimethyl-5-(p-methylphenoxy)pyrazol-4-carboaldoxime O-2-fluoro-6,6-dimethylhept-2-ene-4-ynyl ether;
1,3-Dimethyl-5-(p-methoxyphenoxy)pyrazol-4-carboaldoxime O-2-fluoro-6,6-dimethylhept-2-ene-4-ynyl ether;
1,3-Dimethyl-5-(p-fluorophenoxy)pyrazol-4-carboaldoxime O-2-fluoro-6,6-dimethylhept-2-ene-4-ynyl ether;
1,3-Dimethyl-5-(m-fluorophenoxy)pyrazol-4-carboaldoxime O-2-fluoro-6,6-dimethylhept-2-ene-4-ynyl ether;
1,3-Dimethyl-5-(3,5-difluorophenoxy)pyrazol-4-carboaldoxime O-2-fluoro-6,6-dimethylhept-2-ene-4-ynyl ether;
1,3-Dimethyl-5-phenoxypyrazol-4-carboaldoxime O-2-fluoro-6,6-dimethyl-6-methoxyhex-2-ene-4-ynyl ether;
1,3-Dimethyl-5-(p-methylphenoxy)pyrazol-4-carboaldoxime O-2-fluoro-6,6-dimethyl-6-methoxyhex-2-ene-4-ynyl ether;
1,3-Dimethyl-5-(p-methoxyphenoxy)pyrazol-4-carboaldoxime O-2-fluoro-6,6-dimethyl-6-methoxyhex-2-ene-4-ynyl ether;
1,3-Dimethyl-5-(m-fluorophenoxy)pyrazol-4-carboaldoxime O-2-fluoro-6,6-dimethyl-6-methoxyhex-2-ene-4-ynyl ether;
1,3-Dimethyl-5-sec-butyloxypyrazol-4-carboaldoxime O-2-fluoro-6,6-dimethylhept-2-ene-4-ynyl ether;
1,3-Dimethyl-5-sec-butyloxypyrazol-4-carboaldoxime O-2-fluoro-6,6-dimethyl-6-methoxyhex-2-ene-4-ynyl ether;
1,3-Dimethyl-5-(2,2,3,3,3-pentafluoro-n-propyloxy)-pyrazol-4-carboaldoxime O-2-fluoro-6,6-dimethylhex-2-ene-4-ynyl ether;
1,3-Dimethyl-5-sec-butyloxypyrazol-4-carboaldoxime O-2-fluoro-5trimethylsilylpent-2-ene-4-ynyl ether;
1,3-Dimethyl-5-sec-butyloxypyrazol-4-carboaldoxime O-2-fluoro-6,6-dimethyloct-2-ene-4-ynyl ether;
1,3-Dimethyl-5-cyclohexyloxypyrazol-4-carboaldoxime O-2-fluoro-6,6-dimethylhept-2-ene-4-ynyl ether.

Insect pests against which the present compounds are effective include Hemiptera such as planthoppers, leafhoppers, aphids, bugs, whiteflies, etc.; Lepidoptera such as diamond-back moth (*Plutella xylostella*), rice stem boxer (*Chilo suppressalis*), rice leafroller (*Cnaphalocrocis medinalis*), armyworms and cutworms, Plusiid moths (Plusiinae), small white butterfly (*Pieris rapae crucivora*), casemaking clothes moth (*Tinea pellionella*), webbing clothes moth (*Tineola bisselliella*), etc.; Diptera such as common mosquito (*Culex pipiens pallens*), Anopheline mosquito (Anopheles spp.), Aedes mosquito (Aedes spp.), housefly (*Musca domestica*), etc.; Dictyoptera such as German cockroach (*Blattella germanica*), smokybrown cockroach (*Periplaneta fuliginosa*), brown cockroach (*Periplaneta brunnea*), American cockroach (*Periplaneta americana*), etc.; Coleoptera, Hymenoptera, Thysanoptera, Orthoptera, etc.; and spider mites such as carmine spider mite (*Tetranychus cinnabarinus*), two-spotted spider mite (*Tetranychus urticae*), citrus red mite (*Panonychus citri*), etc. Further, the present compounds are also effective against insect pests having an increased resistance to the existing insecticides and acaricides.

Further, the present compounds exhibit excellent controlling effects in terms of a preventive effect, a curative effect or a systemic effect on various plant diseases.

As plant diseases on which the present compounds have excellent controlling effect, examples are: blast of rice (*Pyricularia oryzae*), helminthosporium leaf spot of rice (*Cochliobolus miyabeanus*), sheath blight of rice (*Rhizoctonia solani*), powdery mildew of wheat and barley (*Erysiphe graminis* f. sp. hordei and E. g. f. sp. tritici), net blotch of wheat and barley (*Pyrenophora teres*), fusarium blight of wheat and barley (*Gibberella zeae*), rust of wheat and barley (*Puccinia striiformis, P. graminis, P. recondita* and *P. hordei*), snow blight of wheat and barley (Typhula sp. and *Micronectriella nivalis*), loose smut of wheat and barley (*Ustilago tritici* and *U. nuda*), bunt of wheat and barley (*Tilletia caries*), eye spot of wheat and barley (*Pseudocercosporella herpotrichoides*), leaf blotch of wheat and barley (*Rhynchosporium secalis*), speckled leaf blotch of wheat and barley (*Septoria tritici*), glume blotch of wheat and barley (*Leptosphaeria nodorum*), melanose of citrus (*Diaporthe citri*), scab of citrus (*Elsinoe fawcetti*), fruit rot of citrus (*Penicillium digitatum* and *P. italicum*), blossom blight of apple (*Sclerotinia mali*), canker of apple (*Valsa mali*), powdery mildew of apple (*Podosphaera leucotricha*), alternaria leaf spot of apple (*Alternaria mali*), scab of apple (*Venturia inaequalis*), scab of pear (*Venturia nashicola* and *V. pirina*), black spot of pear (*Alternaria kikuchiana*), rust of pear (*Gymnosporangium haraeanum*), brown rot of peach (*Sclerotinia cinerea*), scab of peach (*Cladosporium carpophilum*), phomopsis rot of peach (Phomopsis sp.), anthracnose of grape (*Elsinoe ampelina*), ripe rot of grape (*Glomerella cingulata*), powdery mildew of grape (*Uncinula necator*), rust of grape (*Phakopsora ampelopsidis*), black rot of grape (*Guignardia bidwellii*), downy mildew of grape (*Plasmopara viticola*), anthracnose of Japanese persimmon (*Gloeosporium kaki*), leaf spot of Japanese persimmon (*Cercospora kaki* and *Mycosphaerella nawae*), anthracnose of cucumber (*Colletotrichum lagenarium*), powdery mildew of cucumber (*Sphaerotheca fuliginea*), gummy stem blight of cucumber (*Mycosphaerella melonis*), downy mildew of cucumber (*Pseudoperonospora cubensis*), early blight of tomato (*Alternaria solani*), leaf mold of tomato (*Cladosporium fulvum*), late blight of tomato (*Phytophthora infestans*), phomopsis blight of eggplant (*Phomopsis vexans*), powdery mildew of eggplant (*Erysiphe cichoracearum*), alternaria leaf spot of brassica (*Alternaria*

*japonica*), white spot of brassica (*Cercosporella brassicae*), rust of Welsh onion (*Puccinia allii*), purple stain of soybean (*Cercospora kikuchii*), anthracnose of soybean (*Elsinoe glycines*), melanose of soybean (*Diaporthe phaseolorum* var. *sojae*), anthracnose of kidney bean (*Colletotrichum lindemuthianum*), leaf spot of peanut (*Mycosphaerella personatum*), brown leaf spot of peanut (*Cercospora arachidicola*), powdery mildew of pea (*Erysiphe pisi*), early blight of potato (*Alternaria solani*), late blight of potato (*Phytophthora infestans*), powdery mildew of strawberry (*Sphaerotheca humuli*), net blister blight of tea (*Exobasidium reticulatum*), white scab of tea (*Elsinoe leucospila*), brown spot of tobacco (*Alternaria longipes*), powdery mildew of tobacco (*Erysiphe cichoracearum*), anthracnose of tobacco (*Colletorichum tabacum*), cercospora leaf spot of beet (*Cercospora beticola*), scab of rose (*Diplocarpon rosae*), powdery mildew of rose (*Sphaerotheca pannosa*), leaf blight of chrysanthemum (*Septoria chrysanthemiindici*), rust of chrysanthemum (*Puccinia horiana*), gray mold (*Botrytis cinerea*) and stem rot (*Sclerotinia sclerotiorum*) of various crops, and the like.

Of the present compounds, those represented by the following formula (I') can be produced, for example, by the following method A, B or C:

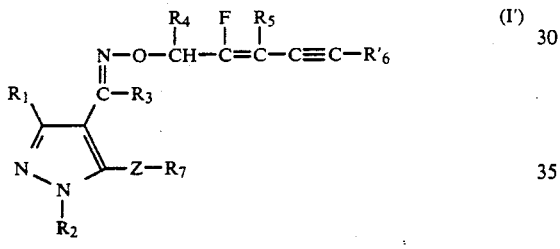

wherein $R_1$, $R_2$, $R_3$, $R_4$, $R_5$, $R_7$ and Z are as defined above; and $R'_6$ is a hydrogen atom, or an alkyl, haloalkyl, alkenyl, alkoxyalkyl or alkylthioalkyl group, or an optionally substituted cycloalkyl, cycloalkenyl, phenyl or pyridyl group.

METHOD A

A method for producing the present compounds (I') compromising reacting a compound represented by the formula (II),

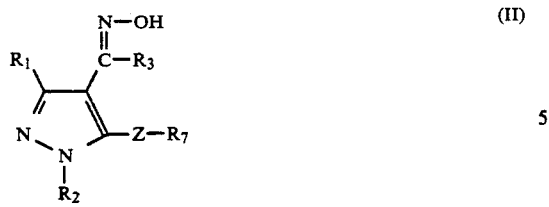

wherein $R_1$, $R_2$, $R_3$, $R_7$ and Z are as defined above, with a compound represented by the formula (III),

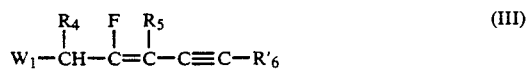

wherein $R_4$, $R_5$ and $R'_6$ are as defined above; and $W_1$ is a halogen atom.

METHOD B

A second method for producing the present compounds (I') compromises reacting a compound represented by the formula (IV),

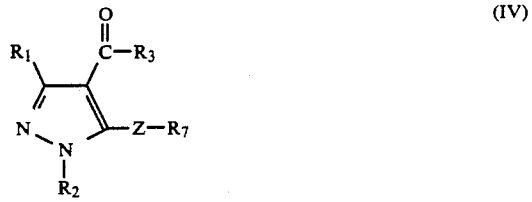

wherein $R_1$, $R_2$, $R_3$, $R_7$ and Z are as defined above, with a compound represented by the formula (V),

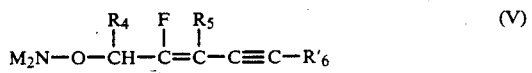

wherein $R_4$, $R_5$ and $R'_6$ are as defined above.

METHOD C

A third method for producing the present compounds (I') compromises reacting a compound represented by the formula (II),

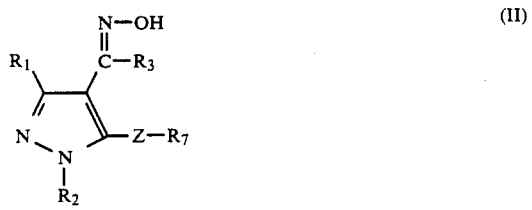

wherein $R_1$, $R_2$, $R_3$, $R_7$ and Z are as defined above, with a compound represented by the formula (VI),

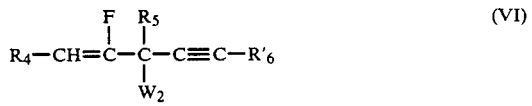

wherein $R_4$, $R_5$ and $R'_6$ are as defined above; and $W_2$ is a halogen atom.

In Methods A and C, a solvent is not always necessary for the reaction, but when a solvent is used, the following solvents are examples of those used: Ethers (e.g. diethyl ether, tetrahydrofuran, dioxane), alcohols (e.g. ethylene glycol, glycerin, methanol, ethanol), acid amides (e.g. N,N-dimethylformamide, N,N-dimethylacetamide), sulfolane, dimethyl sulfoxide, aromatic hydrocarbons (e.g. benzene, toluene, chlorobenzene), halogenated hydrocarbons (e.g. methylene chloride, chloroform), ketones (e.g. acetone, methyl isobutyl ketone), nitriles (e.g. acetonitrile, benzonitrile), pyridines (e.g. pyridine, picoline), water and mixtures of these solvents. The compound of the formula (III) or (VI) is used in an amount of from 0.5 to 10 moles per 1 mole of the compound of the formula (II). The reaction temperature is usually from −20° to 200° C., preferably, from −10° to 100° C. The reaction time is usually from 5 minutes to 100 hours, preferably, from 30 minutes to 50 hours.

Usually, in carrying out this reaction, the following compounds are used as an acid-binding agent: Alkali metal hydroxides (e.g. lithium hydroxide, sodium hydroxide, potassium hydroxide), alkali metal carbonates (e.g. sodium carbonate, potassium carbonate), alkali metal hydrides (e.g. lithium hydride, sodium hydride, potassium hydride), alkali metals (e.g. metallic lithium, metallic sodium, metallic potassium), alkali metal alkoxides (e.g. sodium methoxide, sodium ethoxide) and mixtures thereof. The amount of the acid-binding agent used is from 0.5 to 10 moles for 1 mole of the compound of the formula (II). If necessary, a phase transfer catalyst such as ammonium salts (e.g. tetra-n-butylammonium bromide, benzyltrimethylammonium chloride), ethers (e.g. 18-Crown-6), amines [e.g. tris(3,6-dioxoheptyl)amine (TDA-1)], etc. may also be used in an amount of from 0.0001 to 1 mole per 1 mole of the compound of the formula (II).

After completion of the reaction, the desired present compounds can be obtained by the conventional after-treatments.

In Method B, a solvent is not always necessary for the reaction, but when a solvent is used, the following solvents can be used: Ethers (e.g. diethyl ether, tetrahydrofuran, dioxane), alcohols (e.g. ethylene glycol, glycerin, methanol, ethanol), acid amides (e.g. N,N-dimethylformamide, N,N-dimethylacetamide), sulfolane, dimethyl sulfoxide, aromatic hydrocarbons (e.g. benzene, toleuene, chlorobenzene), halogenated hydrocarbons (e.g. methylene chloride, chloroform), aliphatic hydrocarbons (e.g. pentane, hexane, heptane, cyclohexane), pyridines (e.g. pyridine, picoline), acetic acid, water and mixtures of these solvents. The compound of the formula (V) is used in an amount of from 0.5 to 10 moles per 1 mole of the compound of the formula (IV). The reaction temperature is usually from $-20°$ to $200°$ C., preferably, from $-10°$ to $150°$ C. The reaction time is usually from 5 minutes to 100 hours, preferably, from 5 minutes to 20 hours. If necessary, the following agents may be used as a catalyst for reaction: Mineral acids (e.g. hydrochloric acid, sulfuric acid, nitric acid), organic acids (e.g. formic acid, acetic acid, propionic acid, methanesulfonic acid, benzenesulfonic acid, p-toluenesulfonic acid), amine/acid adducts (e.g. pyridine hydrochloride, triethylamine hydrochloride, morpholine hydrochloride), etc. The amount of the catalyst used is from 0.001 to 1 mole per 1 mole of the compound of the formula (IV).

After completion of the reaction, the desired present compounds can be obtained by the conventional after-treatments.

Of the present compounds, those represented by the following formula (I'') can be produced, for example, by the following method D:

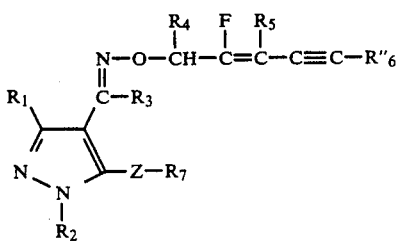

wherein $R_1$, $R_2$, $R_3$, $R_4$, $R_5$, $R_7$ and Z are as defined above; and $R''_6$ is a trialkylsilyl or dialkylphenylsilyl group.

METHOD D:

A method for producing the present compounds (I'') compromising reacting a compound represented by the formula (II''),

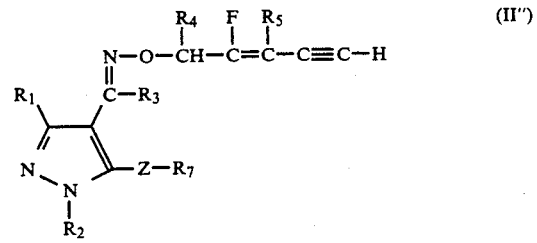

wherein $R_1$, $R_2$, $R_3$, $R_4$, $R_5$, $R_7$ and Z are as defined above, with a trialkylsilyl chloride or a dialkylphenylsilyl chloride.

In Method D, a solvent is usually used. For example, the following solvents are used: Ethers (e.g. diethyl ether, diisopropyl ether, tetrahydrofuran, dioxane), aromatic hydrocarbons (e.g. benzene, toleuen), acid amides (e.g. N,N-dimethylformamide, N,N-dimethylacetamide), sulfolane, dimethyl sulfoxide and mixtures of these solvents. Usually, in carrying out this reaction, a base is used. For example, the following bases are used: Alkyl lithiums (e.g. n-butyl lithium), phenyl lithiums, alkyl magnesium halides (e.g. ethyl magnesium bromide), phenyl magnesium halides, alkali metal hydrides (e.g. lithium hydride, sodium hydride, potassium hydride). The trialkylsilyl chloride or dialkylphenylsilyl chloride is used in an amount of from 0.1 to 10 moles, preferably, from 0.5 to 2 moles per 1 mole of the compound of the formula (I''). The base is used in an amount of from 0.5 to 1.2 moles per 1 mole of the compound of the formula (I''). The reaction temperature is usually from $-100°$ to $200°$ C. The reaction time is usually from five minutes to 100 hours, preferably, from 30 minutes to 50 hours.

After completion of the reaction, the desired present compounds (I'') can be obtained by the conventional after-treatments.

Among the compounds used in Methods A, B and C, the following compounds are novel: compounds (III), (V) and (VI); a compound (VII) represented by the formula (VII), which is included in the scope of the compound (II) for Methods A and C:

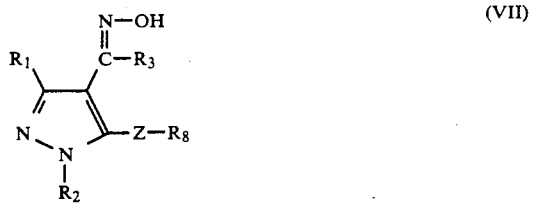

wherein $R_1$, $R_2$, $R_3$ and Z are as defined above, and $R_8$ is an alkyl, haloalkyl, alkenyl, haloalkenyl, alkynyl, haloalkynyl, alkoxyalkyl, alkylthioalkyl or mono or dialkylaminoalkyl group, or an optionally substituted cycloalkyl or cycloalkenyl group, or a group represented by

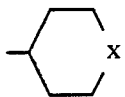

(in which X is an oxygen or sulfur atom); and a compound represented by the formula (VIII), which is included in the scope of the compound (IV) for Method B:

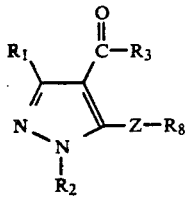

wherein $R_1$, $R_2$, $R_3$, $R_8$ and Z are as defined above.

These compounds may be produced by the following methods.

The compound represented by the formula (III) may be produced, for example, by reacting a compound represented by the formula (IX),

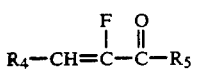

wherein $R_4$ and $R_5$ are as defined above, with a compound represented by the formula (X),

wherein $R'_6$ is as defined above, to obtain a compound represented by the formula (XI),

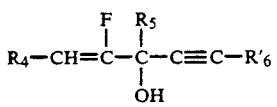

wherein $R_4$, $R_5$ and $R'_6$ are as defined above, and then subjecting the resulting compound (XI) to rearrangement and halogenation.

In carrying out the first step of this reaction, a solvent is usually used. The solvent used includes, ethers (e.g. diethyl ether, diisopropyl ether, tetrahydrofuran, dioxane), aromatic hydrocarbons (e.g. benzene, toluene), alcohols (e.g. ethylene glycol, glycerin, methanol, ethanol), amides (e.g. N,N-dimethylformamide), sulfoxides (e.g. dimethyl sulfoxide, sulfolane), water and mixtures thereof. In this reaction, a base is usually used. The base used includes, alkyllithiums (e.g. n-butyllithium), phenyllithiums, alkylmagnesium halides (e.g. ethylmagnesium bromide), alkali metal hydrides (e.g. lithium hydride, sodium hydride, potassium hydride), alkali metal hydroxides (e.g. lithium hydroxide, sodium hydroxide, potassium hydroxide), alkali metals (e.g. lithium, sodium, potassium), etc.

As to the amounts of the reagents used for the reaction, the amount of the compound of the formula (X) is from 0.1 to 10 moles, preferably, from 0.5 to 2 moles per 1 mole of the compound of the formula (IX), and that of the base is from 0.5 to 10 moles per the same. The reaction temperature is usually from $-100°$ to $300°$ C., and the reaction time is usually from 5 minutes to 100 hours, preferably, from 30 minutes to 50 hours. If necessary, a phase transfer catalyst such as ammonium salts (e.g. tetra-n-butylammonium bromide, benzyltrimethylammonium chloride), ethers (e.g. 18-Crown-6), amines [e.g. tris(3,6-dioxoheptyl)amine (TDA-1)], etc. may be used in an amount of from 0.0001 to 1 mole per 1 mole of the compound of the formula (IX).

After completion of the reaction, the compound of the formula (XI) can be obtained by the conventional after-treatments.

In the second step of the reaction to produce the compound of the formula (III) by the rearrangement and halogenation of the compound of the formula (XI), a solvent may not be necessary. However, when a solvent is used, a solvent such as halogenated hydrocarbons (e.g. methylene chloride, chloroform, dichloroethane), hydrocarbons (e.g. hexane, heptane), aromatic hydrocarbons (e.g. benzene, toluene, chlorobenzene), alcohols (e.g. methanol, ethanol, isopropanol), water and mixtures thereof will usually be used. As the halogenating agent used in the reaction, hydrochloric acid, hydrobromic acid, hydroiodic acid, etc. may be used.

As to the amount of the reagent used for the reaction, the amount of the halogenating agent is from 0.1 to 10 moles, preferably, from 0.5 to 3 moles per 1 mole of the compound of the formula (XI). The reaction temperature is usually from $-30°$ to $200°$ C., preferably, from $-20°$ to $150°$ C.. The reaction time is usually from 5 minutes to 100 hours, preferably, from 30 minutes to 50 hours.

After completion of the reaction, the compound of the formula (III) can be obtained by the conventional after-treatments.

The compound represented by the formula (VI) can be obtained by subjecting the compound represented by the formula (XI) to halogenation.

In carrying out the reaction, a solvent may not be necessary. However, when a solvent is used, a solvent such as halogenated hydrocarbons (e.g. methylene chloride, chloroform, dichloroethane), hydrocarbons (e.g. hexane, heptane), aromatic hydrocarbons (e.g. benzene, toluene, chlorobenzene) and mixtures thereof may be used. As the halogenating agent used in reaction, thionyl chloride etc. may be used.

As to the amount of the reagent used for the reaction, the amount of the halogenating agent is from 0.1 to 10 moles, preferably, from 0.5 to 3 moles per 1 mole of the compound of the formula (XI). The reaction temperature is usually from $-30°$ to $200°$ C., preferably, from $-20°$ to $150°$ C. The reaction time is usually from 5 minutes to 100 hours, preferably, from 30 minutes to 50 hours. If necessary a compound such as amides (e.g. N,N-dimethylformamide), pyridines (e.g. pyridine, picoline), anilines (e.g. N,N-dimethylaniline), aliphatic amines (e.g. triethylamine), etc. may be used in an amount of from 0.0001 to 1 mole per 1 mole of the compound of the formula (XI).

After completion of the reaction, the compound of the formula (VI) can be obtained by the conventional after-treatment.

The compound represented by the formula (V) can be obtained by reacting the compound represented by the formula (III) or (VI) with a compound represented by the formula (XII),

wherein Y is a group represented by

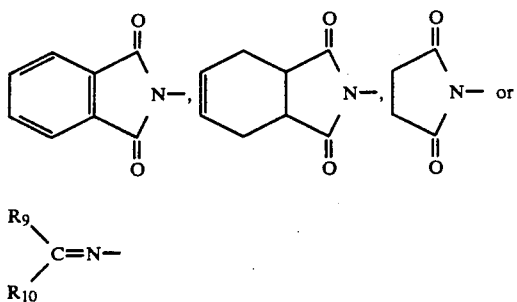

(in which $R_9$ and $R_{10}$, which may be the same or different, are a lower alkyl or phenyl group), to obtain a compound represented by the formula (XIII), $$Y-O-CH-\underset{R_4}{\overset{F}{C}}=\underset{R_5}{C}-C\equiv C-R'_6 \qquad (XIII)$$

wherein Y, $R_4$, $R_5$ and $R'_6$ are as defined above, and reacting the resulting compound (XIII) with, for example, hydroxylamine or hydrazine. Alternatively, the compound (V) can be obtained by reacting the resulting compound (XIII) with, for example, a mineral acid (e.g. hydrochloric acid, sulfuric acid) and then subjecting to neutralization.

When the compound of the formula (III) or (VI) is reacted with the compound of the formula (XII), a solvent is usually used. Such solvents include, for example, amides (e.g. N,N-dimethylformamide, N,N-dimethylacetamide), sulfoxides (e.g. dimethyl sulfoxide), sulfolane, aromatic hydrocarbons (e.g. benzene, toluene, chlorobenzene), halogenated hydrocarbons (e.g. methylene chloride, chloroform, dichloroethane), alcohols (e.g. methanol, ethanol, isopropanol), nitriles (e.g. acetonitrile), pyridines (e.g. pyridine, picoline), water and mixtures thereof. When this reaction is carried out, a base is usually used. Such bases include, for example, alkali metal hydroxides (e.g. lithium hydroxide, sodium hydroxide, potassium hydroxide), alkali metal carbonates (e.g. potassium carbonate, sodium carbonate), alkali metal hydrogencarbonates (e.g. sodium hydrogencarbonate), aliphatic amines (e.g. triethylamine), alkali metal alkoxides (e.g. sodium methylate, sodium ethylate), alkali metal hydrides (e.g. sodium hydride, potassium hydride), etc.

As to the amounts of the reagents used for the reaction, the amount of the compound of the formula (XII) is from 0.1 to 10 moles, preferably, from 0.5 to 2 moles per 1 mole of the compound of the formula (III) or (VI), and that of the base is from 0.5 to 10 moles per the same. The reaction temperature is usually from $-30°$ to $200°$ C., preferably, from $-10°$ to $150°$ C., and the reaction time is usually from 5 minutes to 100 hours, preferably, from 30 minutes to 50 hours.

As an auxiliary for the reaction, for example, a phase transfer catalyst such as ammonium salts (e.g. tetra-n-butylammonium bromide, benzyltrimethylammonium chloride), ethers (e.g. 18-Crown-6), tris (3,6-dioxoheptyl)amine (TDA-1), etc. may be used in an amount of from 0.0001 to 1 mole per 1 mole of the compound of the formula (III) or (VI).

After completion of the reaction, the compound of the formula (XIII) can be obtained by the conventional after-treatments.

When the compound of the formula (XIII) is reacted with hydroxylamine or hydrazine, or with a mineral acid (e.g. hydrochloric acid, sulfuric acid), a solvent is usually used. Such solvents include, alcohols (e.g. methanol, ethanol, isopropanol), aromatic hydrocarbons (e.g. benzene, toluene, chlorobenzene), water and mixtures thereof.

As to the amount of the reagent used for the reaction, the amount of hydroxylamine, hydrazine or a mineral acid (e.g. hydrochloric acid, sulfuric acid) is from 0.5 to 100 moles per 1 mole of the compound of the formula (XIII). The reaction temperature is usually from $0°$ to $300°$ C., and the reaction time is usually from 5 minutes to 200 hours.

If necessary a phase transfer catalyst such as ammonium salts (e.g. tetra-n-butylammonium bromide, benzyltrimethylammonium chloride), ethers (e.g. 18-Crown-6), tris (3,6-dioxoheptyl)amine (TDA-1), etc. may be used in an amount of from 0.0001 to 1 mole per 1 mole of the compound of the formula (XIII).

After completion of the reaction, the desired compound of the formula (V) can be obtained by the liquid-liquid separation of the reaction solution, or by purification and neutralization with an acid (e.g. hydrochloric acid, sulfuric acid) or a base (e.g. sodium hydroxide, potassium hydroxide).

The compound represented by the formula (VIII) can be obtained, for example, by reacting a compound represented by the formula (XIV),

wherein $R_1$, $R_2$ and $R_3$ are as defined above, with a compound represented by the formula (XV),

wherein $R_8$ and Z are as defined above.

In carrying out this reaction, a solvent is not always necessary, but when a solvent is added, for example, the following solvents are used: Ethers (e.g. diethyl ether, tetrahydrofuran, dioxane), alcohols (e.g. ethylene glycol, glycerin, methanol, ethanol), acid amides (e.g. N,N-dimethylformamide, N,N-dimethylacetamide), sulfolane, dimethyl sulfoxide, aromatic hydrocarbons (e.g. benzene, toluene, chlorobenzene), halogenated hydrocarbons (e.g. methylene chloride, chloroform), ketones (e.g. acetone, methyl isobutyl ketone), nitriles (e.g. acetonitrile), pyridines (e.g. pyridine, picoline), water and mixtures of these solvents. The compound of the formula (XV) is used in an amount of from 0.5 to 10 moles per 1 mole of the compound of the formula (XIV). The reaction temperature is usually from $-20°$ to $200°$ C., preferably, from $-10°$ to $100°$ C. The reaction time is usually from 5 minutes to 100 hours, preferably, from 30 minutes to 50 hours.

Usually, in carrying out this reaction, the following compounds are added as an acid-binding agent: Alkali metal hydroxides (e.g. lithium hydroxide, sodium hydroxide, potassium hydroxide), alkali metal carbonates (e.g. sodium carbonate, potassium carbonate), alkali metal hydrides (e.g. lithium hydride, sodium hydride, potassium hydride), alkali metals (e.g. metallic lithium, metallic sodium, metallic potassium), alkali metal alkoxides (e.g. sodium methoxide, sodium ethoxide) and mixtures thereof. The amount of the acid-binding agent used is from 0.5 to 10 moles based on 1 mole of the compound of the formula (XIV). If necessary, as a catalyst for the reaction, a phase transfer catalyst such as ammonium salts (e.g. tetra-n-butylammonium bromide, benzyltrimethylammonium chloride), ethers (e.g. 18-Crown-6), amines [e.g. tris(3,6-dioxo-heptyl)amine (TDA-1)], etc. may be used in an amount of from 0.0001 to 1 mole per 1 mole of the compound of the formula (XIV).

After completion of the reaction, the desired compound of the formula (VIII) can be obtained by the conventional after-treatments.

The compound represented by the formula (VII) can be obtained by reacting the compound represented by the formula (VIII) with a hydroxylamine/acid adduct such as hydroxylamine hydrochloride, hydroxylamine sulfate, etc.

In carrying out this reaction, a solvent is not always necessary, but when a solvent is necessary, the following solvents are used: Ethers (e.g. diethyl ether, tetrahydrofuran, dioxane), alcohols (e.g. ethylene glycol, glycerin, methanol, ethanol), acid amides (e.g. N,N-dimethylformamide, N,N-dimethyulacetamide), sulfolane, dimethyl sulfoxide, aromatic hydrocarbons (e.g. benzene, toluene, chloro-benzene), halogenated hydrocarbons (e.g. methylene chloride, chloroform), aliphatic hydrocarbons (e.g. pentane, hexane, heptane, cyclohexane), pyridines (e.g. pyridine, picoline), acetic acid, water and mixtures of these solvents. The hydroxylamine/acid adduct is used in an amount of from 0.5 to 10 moles per 1 mole of the compound of the formula (VIII). The reaction temperature is usually from −20° to 200° C., preferably, from −10° to 150° C. The reaction time is usually from 5 minutes to 100 hours, preferably, from 5 minutes to 20 hours.

Usually, in carrying out this reaction, the following compounds can be used as an acid-binding agent: Alkali metal hydroxides (e.g. lithium hydroxide, sodium hydroxide, potassium hydroxide), alkali metal carbonates (e.g. sodium carbonate, potassium carbonate), alkali metal hydrides (e.g. lithium hydride, sodium hydride, potassium hydride), alkali metals (e.g. metallic lithium, metallic sodium, metallic potassium), alkali metal alkoxides (e.g. sodium methoxide, sodium ethoxide) and mixtures thereof. The amount of the acid-binding agent used is from 0.5 to 10 moles per 1 mole of the compound of the formula (VIII). If necessary, as a catalyst for the reaction, a phase transfer catalyst such as ammonium salts (e.g. tetra-n-butylammonium bromide, benzyltrimethylammonium chloride), ethers (e.g. 18-Crown-6), amines [e.g. tris(3,6-dioxoheptyl)amine (TDA-1)], etc. may be used in an amount of from 0.0001 to 1 mole per 1 mole of the compound of the formula (VIII).

After completion of the reaction, the desired compound of the formula (VII) can be obtained by the conventional after-treatments. The compounds represented by the formula (XVI), (XVII) and (XVIII)

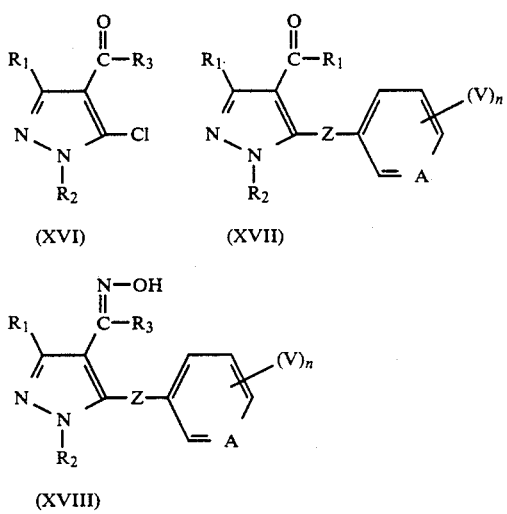

wherein $R_1$, $R_2$, $R_3$, A, V, Z and n are as defined above, are described in EP No. 234,045-A2 234045A2 and JP-A-64-13086.

Examples of the present compounds represented by the formula (I) are, shown in Table 1. Of course, the present invention is not limited to these compounds.

TABLE 1

Compounds represented by the formula:

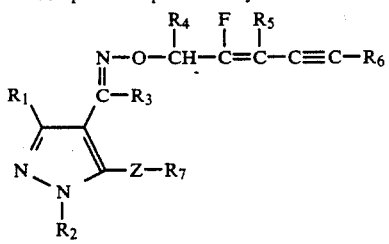

| $R_1$ | $R_2$ | $R_3$ | $R_4$ | $R_5$ | $R_6$ | Z | $R_7$ |
|---|---|---|---|---|---|---|---|
| $CH_3$ | $CH_3$ | H | H | H | $-C(CH_3)_3$ | O | phenyl |

TABLE 1-continued
Compounds represented by the formula:
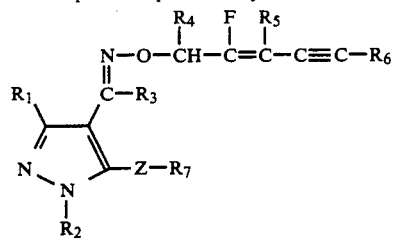
| R₁ | R₂ | R₃ | R₄ | R₅ | R₆ | Z | R₇ |
|---|---|---|---|---|---|---|---|
| CH₃ | CH₃ | H | H | H | −C(CH₃)₃ | O | 4-F-C₆H₄ |
| CH₃ | CH₃ | H | H | H | −C(CH₃)₃ | O | 3-F-C₆H₄ |
| CH₃ | CH₃ | H | H | H | −C(CH₃)₃ | O | 2-F-C₆H₄ |
| CH₃ | CH₃ | H | H | H | −C(CH₃)₃ | O | 4-Cl-C₆H₄ |
| CH₃ | CH₃ | H | H | H | −C(CH₃)₃ | O | 4-CH₃-C₆H₄ |
| CH₃ | CH₃ | H | H | H | −C(CH₃)₃ | O | 4-OCH₃-C₆H₄ |
| −CH₂CH₃ | CH₃ | H | H | H | −C(CH₃)₃ | O | C₆H₅ |
| CH₃ | CH₃ | CH₃ | H | H | −C(CH₃)₃ | O | C₆H₅ |
| CH₃ | −(CH₂)₃CH₃ | H | H | H | −C(CH₃)₃ | O | C₆H₅ |
| CH₃ | −CH(CH₃)₂ | H | H | H | −C(CH₃)₃ | O | C₆H₅ |

TABLE 1-continued
Compounds represented by the formula:
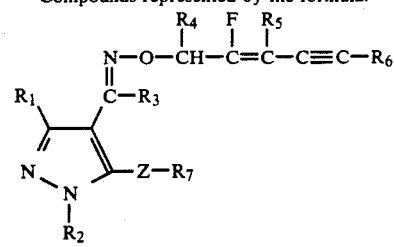
| R₁ | R₂ | R₃ | R₄ | R₅ | R₆ | Z | R₇ |
|---|---|---|---|---|---|---|---|
| CH₃ | CH₃ | H | H | H | 4-CH₃-C₆H₄ | O | C₆H₅ |
| CH₃ | CH₃ | H | H | H | C₆H₅ | O | 4-F-C₆H₄ |
| CH₃ | CH₃ | H | H | H | C₆H₅ | O | 3-F-C₆H₄ |
| CH₃ | CH₃ | H | H | H | C₆H₅ | O | 4-Cl-C₆H₄ |
| CH₃ | CH₃ | H | H | H | C₆H₅ | S | C₆H₅ |
| CH₃ | CH₃ | C₆H₅ | H | H | -C(CH₃)₃ | O | C₆H₅ |
| CH₃ | CH₃ | H | H | H | -C(CH₃)₃ | O | 3,5-F₂-C₆H₃ |
| CH₃ | CH₃ | H | H | H | -C(CH₃)₃ | O | 3-Cl-C₆H₄ |
| CH₃ | CH₃ | H | H | H | -C(CH₃)₃ | S | 4-Cl-C₆H₄ |
| CH₃ | CH₃ | H | H | H | -C(CH₃)₃ | S | 4-CH₃-C₆H₄ |

TABLE 1-continued

Compounds represented by the formula:

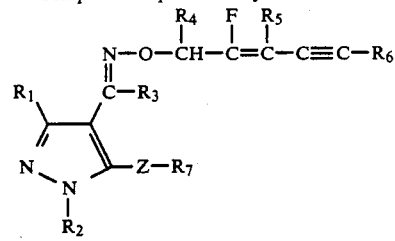

| R₁ | R₂ | R₃ | R₄ | R₅ | R₆ | Z | R₇ |
|---|---|---|---|---|---|---|---|
| CH₃ | CH₃ | H | H | H | phenyl | O | phenyl |
| CH₃ | CH₃ | H | H | H | 4-F-phenyl | O | phenyl |
| CH₃ | CH₃ | H | H | H | —(CH₂)₄CH₃ | O | 4-F-phenyl |
| CH₃ | CH₃ | H | H | H | —C(CH₃)₃ | S | 4-F-phenyl |
| CH₃ | CH₃ | H | H | H | cyclohexyl | S | 4-F-phenyl |
| CH₃ | CH₃ | H | H | H | —CH₂CH₃ | S | 4-F-phenyl |
| CH₃ | CH₃ | H | H | H | —CH₂CH₂CH₂CH₃ | S | 4-F-phenyl |
| —CH₂CH₃ | CH₃ | H | H | H | —C(CH₃)₃ | S | 4-F-phenyl |
| CH₃ | CH₃ | H | H | CH₃ | —C(CH₃)₃ | O | 4-F-phenyl |
| —CH₂CH₃ | CH₃ | H | H | H | —C(CH₃)₃ | O | 4-F-phenyl |
| CH₃ | —CH₂CH₃ | H | H | H | —C(CH₃)₃ | O | 4-F-phenyl |

TABLE 1-continued

Compounds represented by the formula:

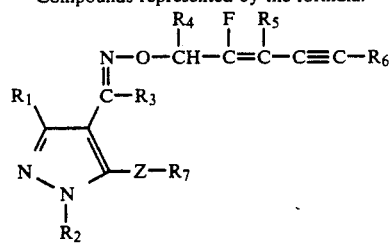

| $R_1$ | $R_2$ | $R_3$ | $R_4$ | $R_5$ | $R_6$ | Z | $R_7$ |
|---|---|---|---|---|---|---|---|
| $CH_3$ | $CH_3$ | H | H | H | $-C(CH_2CH_3)(CH_3)(CH_3)$ | O | 4-F-phenyl |
| $CH_3$ | $CH_3$ | H | H | H | $-C(CH_2CH_3)(CH_3)(CH_2CH_3)$ | O | 4-F-phenyl |
| $CH_3$ | $CH_3$ | H | H | H | $-CH_2CH_2CH_3$ | O | 4-F-phenyl |
| $CH_3$ | $CH_3$ | H | H | H | $-CH(CH_3)_2$ | O | phenyl |
| $CH_3$ | $CH_3$ | H | H | H | $-CH(CH_3)_2$ | O | 4-Cl-phenyl |
| $CH_3$ | $CH_3$ | H | H | H | $-CH(CH_3)_2$ | O | 4-F-phenyl |
| $CH_3$ | $CH_3$ | H | H | H | $-CH(CH_2CH_3)(CH_3)$ | O | phenyl |
| $-CH_2CH_3$ | $CH_3$ | H | H | H | $-C(CH_3)_3$ | S | phenyl |
| $CH_3$ | $CH_3$ | H | $CH_3$ | H | $-C(CH_3)_3$ | O | 4-F-phenyl |
| $CH_3$ | $CH_3$ | H | H | H | $-CH(CH_2CH_3)(CH_2CH_2CH_3)$ | O | phenyl |
| $-(CH_2)_2CH_3$ | $CH_3$ | H | H | H | $-C(CH_3)_3$ | O | phenyl |

TABLE 1-continued

Compounds represented by the formula:

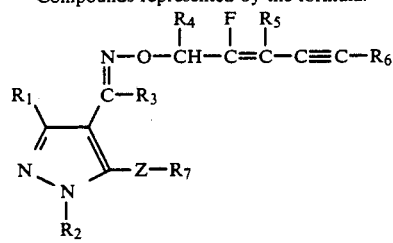

| R1 | R2 | R3 | R4 | R5 | R6 | Z | R7 |
|---|---|---|---|---|---|---|---|
| $-CH(CH_3)_2$ | $CH_3$ | H | H | H | $-C(CH_3)_3$ | O | phenyl |
| $CH_3$ | $CH_3$ | H | H | H | $-C(CH_3)_3$ | S | phenyl |
| $CH_3$ | $CH_3$ | H | H | H | $-C(CH_3)_2CH_2CH_3$ | S | phenyl |
| $CH_3$ | $CH_3$ | H | H | H | cyclohexyl-H | S | phenyl |
| $CH_3$ | $CH_3$ | H | H | H | $CH_3$ | O | phenyl |
| $CH_3$ | $CH_3$ | H | H | H | $-CH_2CH_3$ | O | phenyl |
| $CH_3$ | $CH_3$ | H | H | H | $-CH_2CH_2CH_3$ | O | phenyl |
| $CH_3$ | $CH_3$ | H | H | H | $-CH_2CH_2CH_2CH_3$ | O | phenyl |
| $CH_3$ | $CH_3$ | H | H | H | $-(CH_2)_4CH_3$ | O | phenyl |
| $CH_3$ | $CH_3$ | H | H | H | $-(CH_2)_5CH_3$ | O | phenyl |
| $CH_3$ | $CH_3$ | H | $CH_3$ | H | $-C(CH_3)_3$ | O | phenyl |

TABLE 1-continued
Compounds represented by the formula:
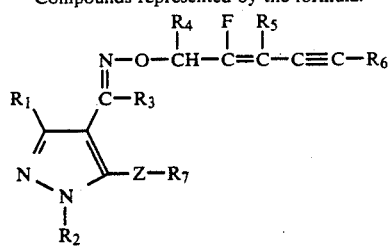
| R1 | R2 | R3 | R4 | R5 | R6 | Z | R7 |
|---|---|---|---|---|---|---|---|
| CH3 | CH3 | H | H | CH3 | −C(CH3)3 | O | phenyl |
| CH3 | CH3 | H | CH3 | H | −C(CH3)3 | O | phenyl |
| CH3 | CH3 | H | H | H | −C(CH3)2CH2CH3 | O | phenyl |
| CH3 | CH3 | H | H | H | cyclohexyl | O | phenyl |
| CH3 | CH3 | H | H | H | 1-methylcyclohexyl | O | phenyl |
| CH3 | CH3 | H | H | H | −C(CH3)3 | O | 3-OCH3-phenyl |
| CH3 | CH3 | H | H | H | −C(CH3)3 | O | 3-CF3-phenyl |
| CH3 | CH3 | H | H | H | −C(CH3)3 | O | 4-OCF2H-phenyl |
| CH3 | CH3 | H | H | H | −C(CH3)3 | O | 3-OCF2H-phenyl |
| CH3 | CH3 | H | H | H | −C(CH3)3 | O | 4-OCF3-phenyl |

TABLE 1-continued

Compounds represented by the formula:

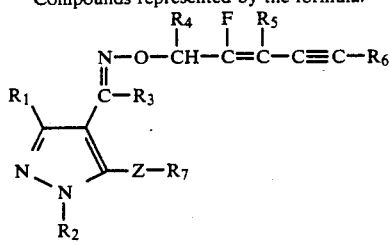

| $R_1$ | $R_2$ | $R_3$ | $R_4$ | $R_5$ | $R_6$ | Z | $R_7$ |
|---|---|---|---|---|---|---|---|
| CH$_3$ | CH$_3$ | H | H | H | -C(CH$_3$)$_3$ | O | 3-OCF$_3$-phenyl |
| CH$_3$ | CH$_3$ | H | H | H | -C(CH$_3$)$_3$ | O | 4-OCF$_2$CF$_2$H-phenyl |
| CH$_3$ | CH$_3$ | H | H | H | -C(CH$_3$)$_3$ | S | 3-CF$_3$-phenyl |
| CH$_3$ | CH$_3$ | H | H | H | -C(CH$_3$)$_3$ | S | 4-OCF$_2$H-phenyl |
| phenyl | CH$_3$ | H | H | H | -C(CH$_3$)$_3$ | O | phenyl |
| CH$_3$ | H | H | H | H | -C(CH$_3$)$_3$ | O | phenyl |
| CH$_3$ | CH$_3$ | H | H | H | -C(CH$_3$)$_3$ | O | 3,4-methylenedioxyphenyl |
| CH$_3$ | -(CH$_2$)$_2$Cl | H | H | H | -C(CH$_3$)$_3$ | O | phenyl |
| CH$_3$ | CH$_3$ | H | H | H | H | O | phenyl |
| CH$_3$ | CH$_3$ | H | H | H | -C(CH$_3$)$_3$ | O | 2,4-dichlorophenyl |

TABLE 1-continued
Compounds represented by the formula:
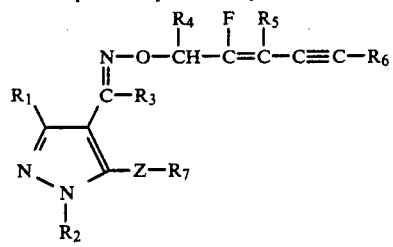
| $R_1$ | $R_2$ | $R_3$ | $R_4$ | $R_5$ | $R_6$ | Z | $R_7$ |
|---|---|---|---|---|---|---|---|
| CH₃ | CH₃ | H | H | H | H | O | 4-Cl-phenyl |
| CH₃ | CH₃ | H | H | H | -C(CH₃)₃ | O | 2,5-dimethylphenyl |
| CH₃ | CH₃ | H | H | H | -C(CH₃)₃ | O | 3-methylphenyl |
| H | CH₃ | H | H | H | -C(CH₃)₃ | O | phenyl |
| CH₃ | CH₃ | H | CH₃ | H | -C(CH₃)₃ | O | phenyl |
| CH₃ | -CH₂CH₃ | H | H | H | -C(CH₃)₃ | O | phenyl |
| CH₃ | -CH₂CH₃ | H | H | H | -C(CH₃)₃ | O | phenyl |
| CH₃ | CH₃ | H | H | H | -C(CH₃)₃ | O | 3-Cl-4-F-phenyl |
| CH₃ | CH₃ | H | H | H | -C(CH₃)₃ | O | 4-Cl-3-methylphenyl |

TABLE 1-continued

Compounds represented by the formula:

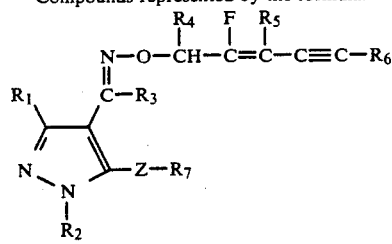

| R₁ | R₂ | R₃ | R₄ | R₅ | R₆ | Z | R₇ |
|---|---|---|---|---|---|---|---|
| CH₃ | CH₃ | H | H | H | -C(CH₃)₃ | O | 4-Cl-3,5-(CH₃)₂-C₆H₂ |
| CH₃ | CH₃ | H | -CH₂CH₃ | H | -C(CH₃)₃ | O | 4-F-C₆H₄ |
| CH₃ | CH₃ | H | H | H | -C(CH₂CH₃)(CH₃)₂ | O | 4-Cl-C₆H₄ |
| CH₃ | CH₃ | H | -n-C₃H₇ | H | -C(CH₃)₃ | O | C₆H₅ |
| CH₃ | CH₃ | H | H | H | -C(CH₂CH₃)(CH₃)₂ | O | 3-F-C₆H₄ |
| -CH₂CH₃ | CH₃ | H | H | H | -C(CH₂CH₃)(CH₃)₂ | O | C₆H₅ |
| -CH₂CH₃ | CH₃ | H | H | H | -C(CH₂CH₃)(CH₃)₂ | O | 4-Cl-C₆H₄ |
| -CH₂CH₃ | CH₃ | H | H | H | -CH(CH₃)₂ | O | 3-F-C₆H₄ |
| -CH₂CH₃ | CH₃ | H | H | H | -CH(CH₃)₂ | O | C₆H₅ |
| -CH₂CH₃ | CH₃ | H | H | H | -CH(CH₃)₂ | O | 4-Cl-C₆H₄ |

TABLE 1-continued

Compounds represented by the formula:

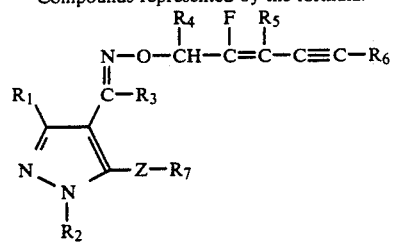

| R₁ | R₂ | R₃ | R₄ | R₅ | R₆ | Z | R₇ |
|---|---|---|---|---|---|---|---|
| $CH_3$ | $CH_3$ | H | H | H | $-CH(CH_3)_2$ | O | phenyl |
| $CH_3$ | $CH_3$ | H | H | H | $-C(CH_3)_3$ | O | 3-pyridyl |
| $CH_3$ | $CH_3$ | H | H | H | $-C(CH_3)_3$ | O | 2-pyridyl |
| $CH_3$ | $CH_3$ | H | H | H | $-C(CH_3)_3$ | O | 6-methyl-3-pyridyl |
| $CH_3$ | $CH_3$ | H | H | H | $-C(CH_3)_3$ | O | 4-tert-butylphenyl |
| $CH_3$ | $CH_3$ | H | H | H | $-Si(CH_3)_3$ | O | phenyl |
| $CH_3$ | $CH_3$ | H | H | H | $-Si(CH_3)_3$ | O | 4-chlorophenyl |
| $CH_3$ | $CH_3$ | H | H | H | $-Si(CH_3)_3$ | O | 4-fluorophenyl |
| $CH_3$ | $CH_3$ | H | H | H | $-Si(CH_3)_3$ | O | 3-fluorophenyl |
| $CH_3$ | $CH_3$ | H | H | H | $-Si(CH_3)_3$ | O | 4-methylphenyl |
| $CH_3$ | $CH_3$ | H | H | H | $-Si(CH_3)_3$ | O | 4-methoxyphenyl |

TABLE 1-continued

Compounds represented by the formula:

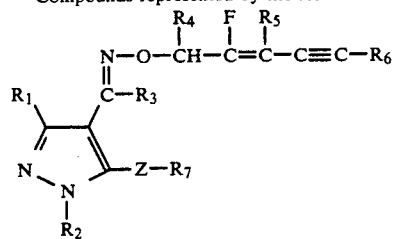

| R₁ | R₂ | R₃ | R₄ | R₅ | R₆ | Z | R₇ |
|---|---|---|---|---|---|---|---|
| CH₃ | CH₃ | H | H | H | -C(CH₃)(CH₃)OCH₃ | O | phenyl |
| CH₃ | CH₃ | H | H | H | -C(CH₃)(CH₃)OCH₃ | O | 4-Cl-phenyl |
| CH₃ | CH₃ | H | H | H | -C(CH₃)(CH₃)OCH₃ | O | 4-F-phenyl |
| CH₃ | CH₃ | H | H | H | -C(CH₃)(CH₃)OC₂H₅ | O | phenyl |
| CH₃ | CH₃ | H | H | H | -C(CH₃)(CH₃)CH₃ | O | cyclohexyl |
| CH₃ | CH₃ | H | H | H | -C(CH₃)(CH₃)CH₃ | O | cyclopentyl |
| CH₃ | CH₃ | H | H | H | -C(CH₃)(CH₃)CH₃ | O | 4-CH₃-cyclohexyl |
| CH₃ | CH₃ | H | H | H | -C(CH₃)(CH₃)CH₃ | O | tetrahydropyran-4-yl |
| CH₃ | CH₃ | H | H | H | -C(CH₃)(CH₃)CH₃ | O | tetrahydrothiopyran-4-yl |
| CH₃ | CH₃ | H | H | H | -C(CH₃)(CH₃)CH₃ | O | -CH(CH₃)₂ |
| CH₃ | CH₃ | H | H | H | -C(CH₃)(CH₃)CH₃ | O | -CH(CH₂CH₃)(CH₃) |

TABLE 1-continued

Compounds represented by the formula:

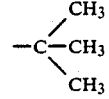

| R₁ | R₂ | R₃ | R₄ | R₅ | R₆ | Z | R₇ |
|---|---|---|---|---|---|---|---|
| CH₃ | CH₃ | H | H | H | -C(CH₃)₃ | O | -CH₂CH₂CH₂CH₃ |
| CH₃ | CH₃ | H | H | H | -C(CH₃)₃ | O | -CH₂(CH₂)₄CH₃ |
| CH₃ | CH₃ | H | H | H | -C(CH₃)₃ | O | -CH₂CH₂CH(CH₃)₂ |
| CH₃ | CH₃ | H | H | H | -C(CH₃)₃ | O | -CH₂CH₂F |
| CH₃ | CH₃ | H | H | H | -C(CH₃)₃ | O | -CH₂CF₃ |
| CH₃ | CH₃ | H | H | H | -C(CH₃)₃ | S | -CH(CH₃)₂ |
| CH₃ | CH₃ | H | H | H | -C(CH₃)₃ | S | -CH₂CH(CH₃)₂ |
| CH₃ | CH₃ | H | H | H | 2-pyridyl | O | phenyl |
| CH₃ | CH₃ | H | H | H | 2-pyridyl | O | -CH(CH₃)₂ |
| CH₃ | CH₃ | H | H | H | 3-pyridyl | O | phenyl |
| CH₃ | CH₃ | H | H | H | -Si(CH₃)₂(phenyl) | O | phenyl |

TABLE 1-continued

Compounds represented by the formula:

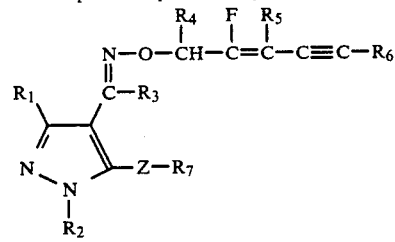

| R₁ | R₂ | R₃ | R₄ | R₅ | R₆ | Z | R₇ |
|---|---|---|---|---|---|---|---|
| CH₃ | CH₃ | H | H | H | −Si(CH₃)(CH₃)(C₆H₅) | O | 4-Cl-C₆H₄ |
| CH₃ | CH₃ | H | H | H | −Si(CH₃)₃ | O | cyclohexyl |
| CH₃ | CH₃ | H | H | H | −Si(CH₃)₃ | O | −CH₂CF₃ |
| CH₃ | CH₃ | H | H | H | −Si(CH₃)(CH₃)(C₆H₅) | O | cyclopentyl |
| CH₃ | CH₃ | H | H | H | −C(CH₃)(CH₃)(OCH₃) | O | −CH(CH₃)₂ |
| CH₃ | CH₃ | H | H | H | −C(CH₃)(CH₃)(OCH₃) | O | cyclohexyl |
| CH₃ | CH₃ | H | H | H | −CH(CF₃)(CH₃) | O | C₆H₅ |
| CH₃ | CH₃ | H | H | H | −CH(CF₃)(CH₃) | O | −CH(CH₂CH₃)(CH₃) |
| CH₃ | CH₃ | H | H | H | −C(CH₃)₃ | O | −CH₂CF₂CF₃ |
| CH₃ | CH₃ | H | H | H | −C(CH₃)₃ | O | −CH₂CF₂CF₂CF₃ |

TABLE 1-continued

Compounds represented by the formula:

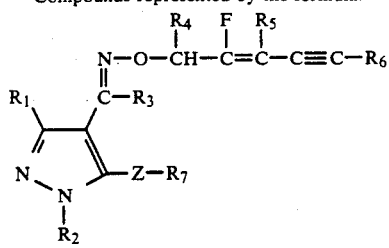

| R₁ | R₂ | R₃ | R₄ | R₅ | R₆ | Z | R₇ |
|---|---|---|---|---|---|---|---|
| CH₃ | CH₃ | H | H | H | −C(CH₃)₃ | O | −CH(CF₃)(CH₃) |
| CH₃ | CH₃ | H | H | H | −C(CH₃)₃ | O | −CH(CF₃)₂ |
| CH₃ | CH₃ | H | H | H | −CH(CH₃)(CF₃) | O | −CH(CF₃)(CH₃) |
| CH₃ | CH₃ | H | H | H | −C(CH₃)₃ | O | −CH₂CH₂SCH₃ |
| CH₃ | CH₃ | H | H | H | −C(CH₃)₃ | O | −CH₂CH₂N(CH₃)₂ |
| CH₃ | CH₃ | H | H | H | cyclohexyl | O | phenyl |
| CH₃ | CH₃ | H | H | H | −C(CH₃)₃ | O | cyclopentyl |
| CH₃ | CH₂F | H | H | H | −C(CH₃)₃ | O | phenyl |
| CH₃ | CH₂F | H | H | H | −C(CH₃)₃ | O | −CH(CH₂CH₃)(CH₃) |
| CH₃ | CH₃ | H | H | H | −C(CH₃)₃ | O | −CH₂CH=CH−CH₃ |
| −CH₂CH₃ | CH₃ | H | H | H | −C(CH₃)₃ | O | −CH(CH₃)₂ |

TABLE 1-continued

Compounds represented by the formula:

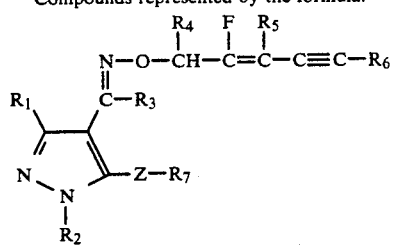

| $R_1$ | $R_2$ | $R_3$ | $R_4$ | $R_5$ | $R_6$ | Z | $R_7$ |
|---|---|---|---|---|---|---|---|
| $CH_3$ | $CH_3$ | H | H | H | $-Si(CH_3)_3$ | O | 3,5-difluorophenyl |
| $-CH_2CH_3$ | $CH_3$ | H | H | H | $-Si(CH_3)_3$ | O | phenyl |
| $-CH_2CH_3$ | $CH_3$ | H | H | H | $-Si(CH_3)_3$ | O | 3,5-difluorophenyl |
| $CH_3$ | $CH_3$ | H | H | H | $-Si(CH_3)_3$ | O | cyclopentyl |
| $CH_3$ | $CH_3$ | H | H | H | $-Si(CH_3)_3$ | O | $-CH_2CF_2CF_3$ |
| $CH_3$ | $CH_3$ | H | H | H | $-Si(CH_3)_3$ | O | $-CH_2CF_2CF_2CF_3$ |
| $CH_3$ | $CH_3$ | H | H | H | $-Si(CH_3)_2Ph$ | O | 4-fluorophenyl |
| $CH_3$ | $CH_3$ | H | H | H | $-Si(CH_3)_2Ph$ | O | 3-fluorophenyl |
| $CH_3$ | $CH_3$ | H | H | H | $-Si(CH_3)_2Ph$ | O | 4-methylphenyl |

TABLE 1-continued

Compounds represented by the formula:

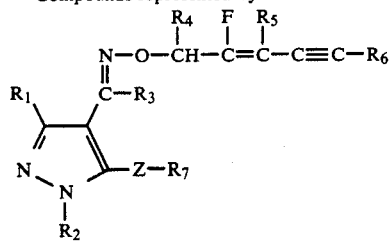

| R₁ | R₂ | R₃ | R₄ | R₅ | R₆ | Z | R₇ |
|---|---|---|---|---|---|---|---|
| CH₃ | CH₃ | H | H | H | H₃C,CH₃ Si-Ph | O | -C₆H₄-OCH₃ (para) |
| -CH₂CH₃ | CH₃ | H | H | H | H₃C,CH₃ Si-Ph | O | -C₆H₅ |
| CH₃ | CH₃ | H | H | H | H₃C,CH₃ Si-Ph | O | cyclohexyl-H |
| CH₃ | CH₃ | H | H | H | H₃C,CH₃ Si-Ph | O | -CH(CH₃)₂ |
| CH₃ | CH₃ | H | H | H | H₃C,CH₃ Si-Ph | O | -CH(CH₂CH₃)(CH₃) |
| CH₃ | CH₃ | H | H | H | H₃C,CH₃ Si-Ph | O | -CH₂CF₃ |
| CH₃ | CH₃ | H | H | H | H₃C,CH₃ Si-Ph | O | -CH₂CF₂CF₃ |
| CH₃ | CH₃ | H | H | H | H₃C,CH₃ Si-Ph | O | -CH₂CF₂CF₂CF₃ |
| CH₃ | CH₃ | H | H | H | H₃C,CH₃ Si-Ph | O | -CH(CH₃)(CF₂CF₃) |

TABLE 1-continued

Compounds represented by the formula:

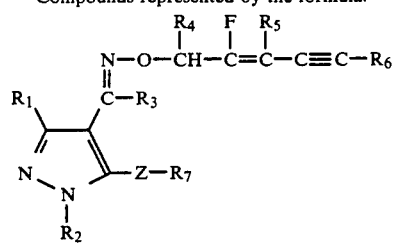

| R1 | R2 | R3 | R4 | R5 | R6 | Z | R7 |
|---|---|---|---|---|---|---|---|
| $CH_3$ | $CH_3$ | H | H | H | -C($CH_3$)($CH_3$)$OCH_3$ | O | 3-F-phenyl |
| $CH_3$ | $CH_3$ | H | H | H | -C($CH_3$)($CH_3$)$OCH_3$ | O | 4-$CH_3$-phenyl |
| $CH_3$ | $CH_3$ | H | H | H | -C($CH_3$)($CH_3$)$OCH_3$ | O | 4-$OCH_3$-phenyl |
| $CH_3$ | $CH_3$ | H | H | H | -C($CH_3$)($CH_3$)$OCH_3$ | O | 3,5-di-F-phenyl |
| $-CH_2CH_3$ | $CH_3$ | H | H | H | -C($CH_3$)($CH_3$)$OCH_3$ | O | phenyl |
| $CH_3$ | $CH_3$ | H | H | H | -C($CH_3$)($CH_3$)$OCH_2CH_2CH_3$ | O | phenyl |
| $CH_3$ | $CH_3$ | H | H | H | -C($CH_3$)($CH_3$)$OCH_3$ | O | -CH($CH_3$)$CH_2CH_3$ |
| $CH_3$ | $CH_3$ | H | H | H | -C($CH_3$)($CH_3$)$OCH_3$ | O | -CH($CH_3$)$CH_2CH_2CH_3$ |
| $CH_3$ | $CH_3$ | H | H | H | -C($CH_3$)($CH_3$)$OCH_3$ | O | cyclopentyl |
| $CH_3$ | $CH_3$ | H | H | H | -C($CH_3$)($CH_3$)$OCH_3$ | O | $-CH_2CF_3$ |

TABLE 1-continued

Compounds represented by the formula:

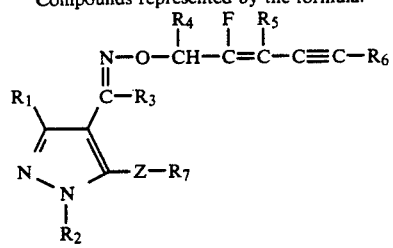

| R1 | R2 | R3 | R4 | R5 | R6 | Z | R7 |
|---|---|---|---|---|---|---|---|
| $CH_3$ | $CH_3$ | H | H | H | $H_3C-\underset{OCH_3}{\underset{|}{C}}-CH_3$ | O | $-CH_2CF_2CF_3$ |
| $CH_3$ | $CH_3$ | H | H | H | $H_3C-\underset{OCH_3}{\underset{|}{C}}-CH_3$ | O | $-CH_2CF_2CF_2CF_3$ |
| $CH_3$ | $CH_3$ | H | H | H | $-C(CH_3)_3$ | O | $-CH(CH_3)CF_2CF_3$ |
| $CH_3$ | $CH_3$ | H | H | H | $-C(CH_3)_3$ | O | $-CH(CH_3)CF_2CF_2CF_3$ |
| $CH_3$ | $CH_3$ | H | H | H | $-C(CH_3)_3$ | O | $-CH_2CF_2CF_2CF_2CF_2H$ |
| $CH_3$ | $CH_3$ | H | H | H | $-C(CH_3)_2CH_2CH_3$ | O | cyclohexyl-H |
| $CH_3$ | $CH_3$ | H | H | H | $-C(CH_3)_2CH_2CH_3$ | O | cyclopentyl-H |
| $CH_3$ | $CH_3$ | H | H | H | $-C(CH_3)_2CH_2CH_3$ | O | $-CH(CH_3)CH_2CH_3$ |
| $CH_3$ | $CH_3$ | H | H | H | $-C(CH_3)_2CH_2CH_3$ | O | $-CH_2CF_3$ |
| $CH_3$ | $CH_3$ | H | H | H | $-C(CH_3)_2CH_2CH_3$ | O | $-CH_2CF_2CF_3$ |
| $CH_3$ | $CH_3$ | H | H | H | $-C(CH_3)_2CH_2CH_3$ | O | $-CH(CH_3)_2$ |
| $CH_3$ | $CH_3$ | H | H | H | $-C(CH_3)_2CH_2CH_3$ | O | $-CH_2CF_2CF_2CF_3$ |

TABLE 1-continued

Compounds represented by the formula:

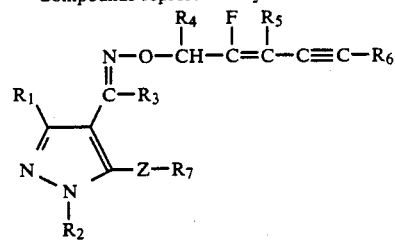

| R₁ | R₂ | R₃ | R₄ | R₅ | R₆ | Z | R₇ |
|---|---|---|---|---|---|---|---|
| —CH₂CH₃ | CH₃ | H | H | H | —C(CH₂CH₃)(CH₃)CH₃ | O | cyclopentyl-H |
| —CH₂CH₃ | CH₃ | H | H | H | —C(CH₂CH₃)(CH₃)CH₃ | O | —CH₂CF₂CF₃ |
| CH₃ | CH₃ | H | H | H | —CH(CH₃)CH₃ | O | cyclohexyl-H |
| CH₃ | CH₃ | H | H | H | —CH(CH₃)CH₃ | O | cyclopentyl-H |
| CH₃ | CH₃ | H | H | H | —CH(CH₃)CH₃ | O | —CH(CH₃)CH₂CH₃ |
| CH₃ | CH₃ | H | H | H | —CH(CH₃)CH₃ | O | —CH₂CH₃ |
| CH₃ | CH₃ | H | H | H | —CH(CH₃)CH₃ | O | —CH₂CF₂CF₃ |
| —CH₂CH₃ | CH₃ | H | H | H | —CH(CH₃)CH₃ | O | cyclohexyl-H |
| —CH₂CH₃ | CH₃ | H | H | H | —CH(CH₃)CH₃ | O | —CH₂CF₂CF₃ |
| CH₃ | CH₃ | H | H | H | —CH(CH₃)CH₃ | O | —CH₂C≡C—C₂H₅ |
| CH₃ | CH₃ | H | H | H | —C(CH₃)(CH₃)CH₃ | O | —CH₂CH(CH₂CH₃)CH₂CH₃ |

TABLE 1-continued

Compounds represented by the formula:

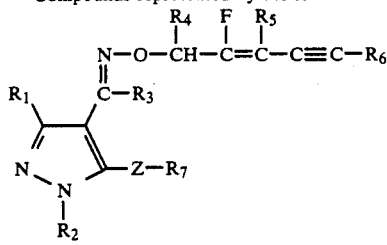

| R1 | R2 | R3 | R4 | R5 | R6 | Z | R7 |
|---|---|---|---|---|---|---|---|
| CH3 | CH3 | H | H | H | -C(CH3)3 | O | CH3 |
| CH3 | CH3 | H | H | H | cyclohexyl(H) | O | -CH(CH2CH3)CH3 |
| CH3 | CH3 | H | H | H | cyclohexyl(H) | O | -CH2CH2CH2CH3 |
| CH3 | CH3 | H | H | H | cyclohexyl(H) | O | -CH2CF3 |
| CH3 | CH3 | H | H | H | cyclohexyl(H) | O | -CH(CH3)2 |
| CH3 | CH3 | H | H | H | cyclohexyl(H) | O | -CH2CF2CF3 |
| CH3 | CH3 | H | H | H | phenyl | O | 4-CH3-phenyl |
| CH3 | CH3 | H | H | H | phenyl | O | 4-OCH3-phenyl |
| CH3 | CH3 | H | H | H | phenyl | O | 3-OCH3-phenyl |
| CH3 | CH3 | H | H | H | phenyl | O | -CH2CF2CF3 |
| CH3 | CH3 | H | H | H | phenyl | O | -CH2CF2CF2CF3 |

TABLE 1-continued

Compounds represented by the formula:

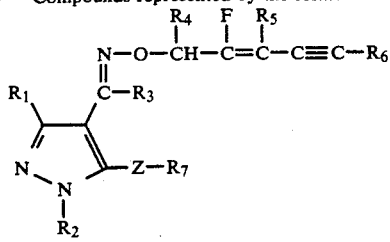

| R₁ | R₂ | R₃ | R₄ | R₅ | R₆ | Z | R₇ |
|---|---|---|---|---|---|---|---|
| CH₃ | CH₃ | H | H | H | —⟨phenyl⟩ | O | ⟨cyclohexyl-H⟩ |
| CH₃ | CH₃ | H | H | H | —C(CH₃)=CH₂ | O | ⟨phenyl⟩ |
| CH₃ | CH₃ | H | H | H | —C(CH₃)=CH₂ | O | ⟨phenyl-CH₃⟩ |
| CH₃ | CH₃ | H | H | H | —C(CH₃)=CH₂ | O | ⟨phenyl-OCH₃⟩ |
| CH₃ | CH₃ | H | H | H | —C(CH₃)=CH₂ | O | ⟨phenyl-F⟩ |
| CH₃ | CH₃ | H | H | H | —C(CH₃)=CH₂ | O | ⟨phenyl-F (meta)⟩ |

When the present compounds are used as an active ingredient for insecticidal, acaricidal and fungicidal compositions, they may be used as they are, without adding any other ingredients. Usually, however, they are formulated into oil sprays, emulsifiable concentrates, wettable powders, flowable concentrates, granules, dusts, aerosols, poisonous baits, etc. by mixing with solid carriers, liquid carriers, gaseous carriers, baits and if necessary, surface active agents and other auxiliaries for formulation.

These formulations contain the present compounds as an active ingredient in an amount of, usually, from 0.01 to 95% by weight.

The solid carriers used in the formulation include fine powders or granules of clays (e.g. kaolin clay, diatomaceous earth, synthetic hydrated silicon dioxide, bentonite, Fubasami clay, terra abla), talcs, ceramics, other inorganic minerals (e.g. sericite, quartz, sulfur, activated carbon, calcium carbonate, hydrated silica), chemical fertilizers (e.g. ammonium sulfate, ammonium phosphate, ammonium nitrate, urea, ammonium chloride), etc. The liquid carriers include water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. hexane, cyclohexane, kerosene, gas oil), esters (e.g. ethyl acetate, butyl acetate), nitriles (e.g. acetonitrile, isobutyronitrile), ethers (e.g. diisopropyl ether, dioxane), acid amides (e.g. N,N-dimethylformamide, N,N-dimethylacetamide), halogenated hydrocarbons (e.g. dichloromethane, trichloroethane, carbon tetrachloride), dimethyl sulfoxide, vegetable oils (e.g. soybean oil, cotton seed oil), etc. The gaseous carriers, i.e. propellants, include, freon gas, butane gas, LPG (liquefied petroleum gas), dimethyl ether, carbon dioxide gas, etc.

The surface active agents used for emulsification, dispersion, wetting, etc. include anionic surface active agents such as the salts of alkyl sulfates, alkyl(aryl)sulfonates, dialkyl sulfosuccinates, the salt of polyoxyethylene alkylaryl ether phosphoric acid esters, naphthalenesulfonic acid/formalin condensates, etc., and nonionic surface active agents such as polyoxyethylene alkyl ether, polyoxyethylene polyoxypropylene block copolymers, sorbitan fatty acid esters, polyoxyethylene sorbitan fatty acid esters, etc.

The auxiliaries for formulation such as fixing agents, dispersing agents, etc. include casein, gelatin, polysaccharides (e.g. starch powder, gum arabic, cellulose derivatives, alginic acid), lignin derivatives, bentonite, saccharides, synthetic water-soluble high polymers (e.g. polyvinyl alcohol, polyvinyl pyrrolidone, polyacrylic acids), etc. The stabilizing agents include PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, surface active agents, fatty acids and their esters, etc.

The base for the poisonous baits includes bait components (e.g. grain powders, vegetable essential oils, saccharides, crystalline celluloses), antioxidants (e.g. dibutylhydroxytoluene, nordihydroguaiaretic acid), preservatives (e.g. dehydroacetic acid), attractants (e.g. cheese perfume, onion perfume), etc. Further, red pepper powders, etc. may also be included as an agent for preventing children from eating the bait mistake.

The flowable formulations (water-based suspension formulations or water-based emulsion formulations) are generally obtained by finely dispersing 1 to 75% of the active ingredient compound in water containing 0.5 to 15% of a dispersing agent, 0.1 to 10% of a suspension auxiliary (e.g. protective colloids, compounds giving a thixotropic property) and 0 to 10% of a suitable auxiliary (e.g. defoaming agents, anticorrosives, stabilizing agents, spreading agents, penetration auxiliaries, antifreezing agents, antibacterial agents, antimolding agents). It is also possible to obtain oil-based suspension formulations by replacing the water by an oil in which the active ingredient compounds are almost insoluble. The protective colloids include, gelatin, casein, gums, cellulose ethers, polyvinyl alcohol, etc., and the compounds giving a thixotropic property include bentonite, aluminum magnesium silicate, xanthane gum, polyacrylic acid, etc.

The formulations thus obtained are used as they are or diluted with water, etc. Further, they may be used in mixtures with other insecticides, acaricides, nematocides, soil-pest controlling agents, pest-controlling agents, fungicides, herbicides, plant growth regulators, synergists, fertilizers, soil improvers, etc., or may be used simultaneously with these chemicals without mixing.

When the present compounds are used as active ingredients for agricultural insecticidal and acaricidal compositions, the dosage rate of the active ingredient is usually from 1 to 1,000 g/10 ares. When the emulsifiable concentrates, wettable powders, flowable concentrates, etc. are used in dilution with water, the application concentration of the active ingredient is from 10 to 1,000 ppm. The granules, dusts, etc. are used as they are without being diluted. When the present compounds are used as household and public hygienic insecticidal and acaricidal compositions, the emulsifiable concentrates, wettable powders, flowable concentrates, etc. are applied diluted with water to from 10 to 1,000 ppm, and the oil sprays, aerosols, poisonous baits, etc. are applied as they are.

When the present compounds are used as active ingredients for fungicidal compositions the dosage rate of the active ingredient is usually from 1 to 1,000 g/10 ares. When the emulsifiable concentrates, wettable powders, flowable concentrates, etc. are used in dilution with water, the application concentration of the active ingredient is from 10 to 100,000 ppm. The granules, dusts, etc. are used as they are without being diluted.

The present compounds are also used as seed disinfectants.

Although any of these dosage rates and application concentrations may vary with the kind of formulations, when, where and how these formulations are applied, the kind of pests, the degree of damage, etc., they may be increased or decreased independently of the ranges explained above.

The present invention will be illustrated in more detail with reference to the following production examples, formulation examples and test examples, but it is not limited to these examples.

First, the production examples will be shown.

PRODUCTION EXAMPLE 1

(Method A)

One gram (0.0043 mole) of 1,3-dimethyl-5-phenoxypyrazol-4-carboaldoxime was added to 10 ml of an N,N-dimethylfomamide solution containing 0.11 g (0.0046 mole) of sodium hydride, and the mixture was stirred at room temperature for 3 hours. Thereafter, 1.53 g (0.007 mole) of 1-bromo-2fluoro-6,6-dimethylhept-2-ene-4-yne was added under ice-cooling, and the mixture was stirred at room temperature for 3 hours. The reaction mixture was poured into 100 ml of ice water and extracted with three 50-ml portions of ethyl acetate. The organic layers were combined, washed once with 100 ml of a saturated aqueous sodium chloride solution and concentrated under reduced pressure. The residue was subjected to column chromatography on silica gel to obtain 0.36 g of 1,3-dimethyl-5-phenoxypyrazol-4-carboaldoxime O-2-fluoro-6,6-dimethylhept-2-ene-4-ynyl ether.

m.p. 57°–58° C.

PRODUCTION EXAMPLE 2

(Method C)

One gram (0.0043 mole) of 1,3-dimethyl-5-phenoxypyrazol-4-carboaldoxime was added to 10 ml of an N,N-dimethylformamide solution containing 0.11 g (0.0046 mole) of sodium hydride, and the mixture was stirred at room temperature for 3 hours. Thereafter, 0.89 g (0.0052 mole) of 3-chloro-6,6-dimethyl-6methoxyhex-1-ene-4-yne was added under ice-cooling, and the mixture was stirred at room temperature for 3 hours. The reaction mixture was poured into 100 ml of ice water and extracted with three 50-ml portions of ethyl acetate. The organic layers were combined, washed once with 100 ml of a saturated aqueous sodium chloride solution and concentrated under reduced pressure. The residue was subjected to column chromatography on silica gel to obtain 0.21 g of 1,3-dimethyl-5-phenoxypyrazol-4-carboaldoxime O-2-fluoro-6,6-dimethyl-6-methoxyhex-2-ene-4-ynyl ether.

$n_D^{24.5}$ 1.5331.

PRODUCTION EXAMPLE 3

(Method A)

One gram (0.0043 mole) of 1,3-dimethyl-5-phenoxypyrazol-4-carboaldoxime was added to 10 ml of an N,N-dimethylformamide solution containing 0.11 g (0.0046 mole) of sodium hydride, and the mixture was stirred at room temperature for 3 hours. Thereafter, 0.61 g (0.0052 mole) of 1-chloro-2-fluoropent-2-ene-4- yne was added under ice-cooling, and the mixture was stirred at room temperature for 3 hours. The reaction mixture was poured into 100 ml of ice water and extracted with three 50-ml portions of ethyl acetate. The organic layers were combined, washed once with 100 ml of a saturated aqueous sodium chloride solution and concentrated under reduced pressure. The residue was subjected to column chromatography on silica gel to obtain 0.31 g of 1,3-dimethyl-5-phenoxypyrazol-4-carboaldoxime O-2-fluoropent-2-ene-4-ynyl ether.

$n_D^{25.5}$ 1.5492.

PRODUCTION EXAMPLE 4

(Method A)

One gram (0.0042 mole) of 1,3-dimethyl-5-cyclohexyloxypyrazol-4-carboaldoxime was added to 10 ml of an N,N-dimethylformamide solution containing 0.11 g (0.0046 mole) of sodium hydride, and the mixture was stirred at room temperature for 3 hours. Thereafter, 1.1 g (0.005 mole) of 1-bromo-2-fluoro-6,6-dimethylhept-2-ene-4-yne was added under ice-cooling, and the mixture was stirred at room temperature for 3 hours. The reaction mixture was poured into 100 ml of ice water and extracted with three 50-ml portions of ethyl acetate. The organic layers were combined, washed once with 100 ml of a saturated aqueous sodium chloride solution and concentrated under reduced pressure. The residue was subjected to column chromatography on silica gel to obtain 0.27 g of 1,3-dimethyl-5-cyclohexyloxypyrazol-4-carboaldoxime O-2-fluoro-6,6-dimethylhept-2-ene-4-ynyl ether.

$n_D^{25.0}$ 1.5159.

PRODUCTION EXAMPLE 5

(Method A)

One gram (0.0035 mole) of 1,3-dimethyl-5-(2,2,3,3,3-pentafluoro)propyloxypyrazol-4-carboaldoxime was added to 10 ml of an N,N-dimethylformamide solution containing 92 mg (0.0038 mole) of sodium hydride, and the mixture was stirred at room temperature for 3 hours. Thereafter, 0.92 g (0.0042 mole) of 1-bromo-2-fluoro-6,6-dimethylhept-2-ene-4-yne was added under ice-cooling, and the mixture was stirred at room temperature for 3 hours. The reaction mixture was poured into 100 ml of ice water and extracted with three 50-ml portions of ethyl acetate. The organic layers were combined, washed once with 100 ml of a saturated aqueous sodium chloride solution and concentrated under reduced pressure. The residue was subjected to column chromatography on silica gel to obtain 0.31 g of 1,3-dimethyl-5-(2,2,3,3,3-pentafluoro)propyloxypyrazol-4-carboaldoxime O-2-fluoro-6,6-dimethylhept-2-ene-4-ynyl ether.

$n_D^{23.0}$ 1.4561.

PRODUCTION EXAMPLE 6

(Method B)

One gram (0.0040 mole) of 1,3-dimethyl-5-(p-chlorophenoxy)pyrazol-4-carboaldehyde was dissolved in 10 ml of methanol', 0.75 g (0.0044 mole) of 2-fluoro-6,6-dimethylhept-2-ene-4-ynyloxyamine was added to the resulting solution. Thereafter, a catalytic amount of a hydrogen chloride gas was bubbled into the reaction solution, and the reaction mixture was aged overnight at room temperature. The reaction mixture was poured into 100 ml of ice water and extracted with three 50-ml portions of ethyl acetate. The organic layers were combined, washed once with 100 ml of a saturated aqueous sodium chloride solution and concentrated under reduced pressure. The residue was subjected to column chromatography on silica gel to obtain 0.23 g of 1,3-dimethyl-5-(p-chlorophenoxy)pyrazol-4-carboaldehydeoxime O-2-fluoro-6,6-dimethyl-hept-2-ene-4-ynyl ether.

$n_D^{26.0}$ 1.5431.

PRODUCTION EXAMPLE 7

(Method D)

0.5 grams (0.0017 mole) of 1,3-dimethyl-5-phenoxypyrazol-4-carboaldehydeoxime O-2-fluoropenta-2-ene-4-yne was dissolved in 10 ml of anhydrous tetrahydrofurane. 1.13 ml of 1.5M hexane solution of n-butyllithium was added to the resulting solution at −60° C. at −60° C. or less under cooling in a dry ice-acetone bath. The reaction mixture was aged for 30 minutes at −60° C. or less. Thereafter, 0.22 g (0.002 mole) of trimethylsilylchloride was added at −60° C. or less. The reaction solution was aged overnight and then was poured into 100 ml of ice water and extracted with three 50 ml portions of ethyl acetate. The organic layers were combined, washed once with 100 ml of a saturated aqueous sodium chloride solution and concentrated under reduced pressure. The residue was subjected to column chromatography on silica gel to obtain 0.13 g of 1,3-dimethyl-5-phenoxypyrazol-4-carboaldehydeoxime O-2-fluoro-5-trimethylsilylpenta-2-ene-4-ynyl ether.

$n_D^{25.0}$ 1.5239.

Some of the present compounds thus obtained are shown in Table 2.

TABLE 2

Compounds represented by the formula

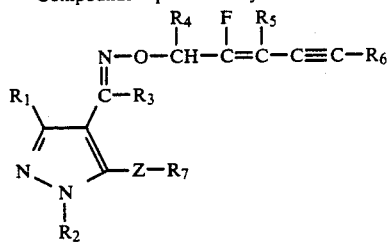

| Compound No. | $R_1$ | $R_2$ | $R_3$ | $R_4$ | $R_5$ | $R_6$ | Z | $R_7$ | Physical Properties |
|---|---|---|---|---|---|---|---|---|---|
| (1) | $CH_3$ | $CH_3$ | H | H | H | $-C(CH_3)_3$ | O | phenyl | m.p. 57–58° C. |
| (2) | $CH_3$ | $CH_3$ | H | H | H | $-C(CH_3)_3$ | O | 4-F-phenyl | m.p. 73–74° C. |
| (3) | $CH_3$ | $CH_3$ | H | H | H | $-C(CH_3)_3$ | O | 3-F-phenyl | $n_D^{28.0}$ 1.5285 |
| (4) | $CH_3$ | $CH_3$ | H | H | H | $-C(CH_3)_3$ | O | 2-F-phenyl | $n_D^{27.5}$ 1.5288 |
| (5) | $CH_3$ | $CH_3$ | H | H | H | $-C(CH_3)_3$ | O | 4-Cl-phenyl | $n_D^{28.0}$ 1.5431 |
| (6) | $CH_3$ | $CH_3$ | H | H | H | $-C(CH_3)_3$ | O | 4-$CH_3$-phenyl | $n_D^{26.5}$ 1.5332 |
| (7) | $CH_3$ | $CH_3$ | H | H | H | $-C(CH_3)_3$ | O | 4-$OCH_3$-phenyl | $n_D^{26.0}$ 1.5395 |
| (8) | $-CH_2CH_3$ | $CH_3$ | H | H | H | $-C(CH_3)_3$ | O | phenyl | m.p. 91.4° C. |
| (9) | $CH_3$ | $CH_3$ | $CH_3$ | H | H | $-C(CH_3)_3$ | O | phenyl | m.p. 117.2° C. |
| (10) | $CH_3$ | $-CH_2CH_3$ | H | H | H | $-C(CH_3)_3$ | O | phenyl | $n_D^{29.0}$ 1.5355 |

TABLE 2-continued

Compounds represented by the formula

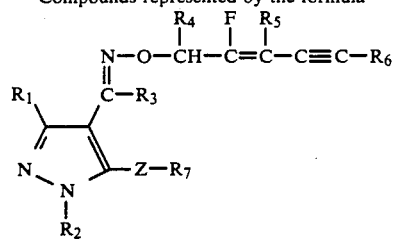

| Compound No. | R₁ | R₂ | R₃ | R₄ | R₅ | R₆ | Z | R₇ | Physical Properties |
|---|---|---|---|---|---|---|---|---|---|
| (11) | $CH_3$ | $CH_3$ | H | H | H | $-C(CH_3)_3$ | S | phenyl | m.p. 95.5° C. |
| (12) | $CH_3$ | $CH_3$ | H | H | H | $-C(CH_3)_3$ | S | 4-F-phenyl | m.p. 95.3° C. |
| (13) | $CH_3$ | $CH_3$ | H | H | H | $-C(CH_3)_3$ | S | 4-Cl-phenyl | $n_D^{25.0}$ 1.5727 |
| (14) | $CH_3$ | $CH_3$ | H | H | H | $-C(CH_3)_3$ | O | 3-Cl-4-F-phenyl | $n_D^{28.0}$ 1.5378 |
| (15) | $CH_3$ | $CH_3$ | H | H | H | $-C(CH_3)_3$ | O | 3-Cl-phenyl | $n_D^{28.0}$ 1.5425 |
| (16) | $CH_3$ | $CH_3$ | H | H | H | $-n-C_6H_{13}$ | O | phenyl | $n_D^{28.0}$ 1.5322 |
| (17) | $CH_3$ | $CH_3$ | H | H | H | cyclohexyl | O | phenyl | m.p. 71.8° C. |
| (18) | $CH_3$ | $CH_3$ | H | $-n-C_3H_7$ | H | $-C(CH_3)_3$ | O | phenyl | $n_D^{28.0}$ 1.5247 |
| (19) | $CH_3$ | $CH_3$ | H | H | H | $-C(CH_3)_3$ | O | 3-$CF_3$-phenyl | $n_D^{26.3}$ 1.5091 |
| (20) | $CH_3$ | $CH_3$ | H | H | H | $-C(CH_3)_3$ | O | 4-Cl-3-$CH_3$-phenyl | $n_D^{24.5}$ 1.5451 |

TABLE 2-continued

Compounds represented by the formula

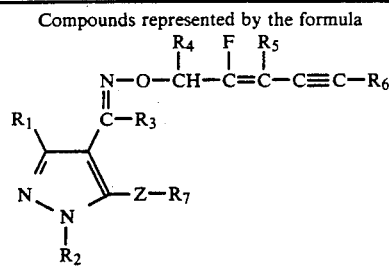

| Compound No. | $R_1$ | $R_2$ | $R_3$ | $R_4$ | $R_5$ | $R_6$ | Z | $R_7$ | Physical Properties |
|---|---|---|---|---|---|---|---|---|---|
| (21) | $CH_3$ | $CH_3$ | H | H | H | $-C(CH_3)_3$ | O | 3-methylphenyl | $n_D^{25.5}$ 1.5392 |
| (22) | $CH_3$ | $CH_3$ | H | H | H | $-C(CH_3)_3$ | O | 4-chloro-3,5-dimethylphenyl | $n_D^{23.0}$ 1.5462 |
| (23) | $CH_3$ | $CH_3$ | H | H | H | $-C(CH_3)_3$ | O | 3,5-dimethylphenyl | $n_D^{23.0}$ 1.5391 |
| (24) | $CH_3$ | $CH_3$ | H | $-CH_2CH_3$ | H | $-C(CH_3)_3$ | O | 4-fluorophenyl | $n_D^{24.0}$ 1.5248 |
| (25) | $CH_3$ | $CH_3$ | H | H | H | $-C(CH_3)_3$ | O | 3,4-methylenedioxyphenyl | $n_D^{22.0}$ 1.5459 |
| (26) | $CH_3$ | $CH_3$ | H | H | H | $-C(CH_3)_3$ | O | 3,5-difluorophenyl | $n_D^{22.0}$ 1.5295 |
| (27) | $CH_3$ | $CH_3$ | H | H | H | $-C(CH_3)_3$ | O | 4-($OCF_2CF_2H$)phenyl | $n_D^{23.0}$ 1.5051 |
| (28) | $CH_3$ | $CH_3$ | H | $CH_3$ | H | $-C(CH_3)_3$ | O | phenyl | $n_D^{25.0}$ 1.5298 |
| (29) | $CH_3$ | $CH_3$ | H | $CH_3$ | H | $-C(CH_3)_3$ | O | 4-fluorophenyl | $n_D^{21.0}$ 1.5305 |

TABLE 2-continued

Compounds represented by the formula $$\begin{array}{c} R_4 \; F \; R_5 \\ N-O-CH-C=C-C\equiv C-R_6 \\ \parallel \\ R_1 \quad C-R_3 \\ \diagdown \diagup \\ N \quad Z-R_7 \\ \diagdown N \diagup \\ \mid \\ R_2 \end{array}$$

| Compound No. | $R_1$ | $R_2$ | $R_3$ | $R_4$ | $R_5$ | $R_6$ | Z | $R_7$ | Physical Properties |
|---|---|---|---|---|---|---|---|---|---|
| (30) | CH$_3$ | CH$_3$ | H | H | H | $-C(CH_3)_3$ | O | 3-pyridyl | $n_D^{23.0}$ 1.5425 |
| (31) | CH$_3$ | CH$_3$ | H | H | H | $-C(CH_3)_3$ | O | 2-pyridyl | $n_D^{19.1}$ 1.5381 |
| (32) | CH$_3$ | CH$_3$ | H | H | H | $-C(CH_3)_3$ | O | 6-methyl-3-pyridyl | $n_D^{25.0}$ 1.5342 |
| (33) | CH$_3$ | CH$_3$ | H | H | H | $-C(CH_3)_3$ | O | 4-(t-butyl)phenyl | $n_D^{25.0}$ 1.5329 |
| (34) | CH$_3$ | CH$_3$ | H | H | H | $-Si(CH_3)_3$ | O | phenyl | $n_D^{24.7}$ 1.5369 |
| (35) | CH$_3$ | CH$_3$ | H | H | H | $-C(CH_3)_2 OCH_3$ | O | phenyl | $n_D^{24.5}$ 1.5331 |
| (36) | CH$_3$ | CH$_3$ | H | H | H | $-C(CH_3)_3$ | O | cyclohexyl | $n_D^{25.0}$ 1.5159 |
| (37) | CH$_3$ | CH$_3$ | H | H | H | $-C(CH_3)_3$ | O | cyclopentyl | $n_D^{24.0}$ 1.5189 |
| (38) | CH$_3$ | CH$_3$ | H | H | H | $-C(CH_3)_3$ | O | 4-methylcyclohexyl | $n_D^{25.0}$ 1.5130 |
| (39) | CH$_3$ | CH$_3$ | H | H | H | $-C(CH_3)_3$ | O | tetrahydropyran-4-yl | $n_D^{24.7}$ 1.5112 |
| (40) | CH$_3$ | CH$_3$ | H | H | H | $-C(CH_3)_3$ | O | tetrahydrothiopyran-4-yl | $n_D^{26.6}$ 1.5150 |

TABLE 2-continued

Compounds represented by the formula

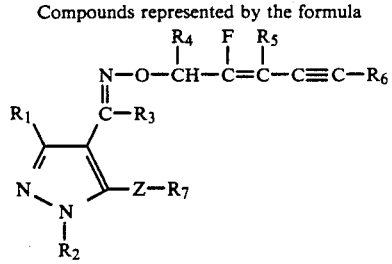

| Compound No. | $R_1$ | $R_2$ | $R_3$ | $R_4$ | $R_5$ | $R_6$ | Z | $R_7$ | Physical Properties |
|---|---|---|---|---|---|---|---|---|---|
| (41) | $CH_3$ | $CH_3$ | H | H | H | $-C(CH_3)_3$ | O | $-CH(CH_3)_2$ | $n_D^{22.0}$ 1.5055 |
| (42) | $CH_3$ | $CH_3$ | H | H | H | $-C(CH_3)_3$ | O | $-CH(CH_3)CH_2CH_3$ | $n_D^{25.5}$ 1.5061 |
| (43) | $CH_3$ | $CH_3$ | H | H | H | $-C(CH_3)_3$ | O | $-CH_2CH_2CH_2CH_3$ | $n_D^{24.0}$ 1.5049 |
| (44) | $CH_3$ | $CH_3$ | H | H | H | $-C(CH_3)_3$ | O | $-(CH_2)_5CH_3$ | $n_D^{24.0}$ 1.5005 |
| (45) | $CH_3$ | $CH_3$ | H | H | H | $-C(CH_3)_3$ | O | $-CH_2CH_2CH(CH_3)_2$ | $n_D^{24.0}$ 1.4973 |
| (46) | $CH_3$ | $CH_3$ | H | H | H | $-C(CH_3)_3$ | O | $-CH_2CH_2F$ | $n_D^{22.0}$ 1.5065 |
| (47) | $CH_3$ | $CH_3$ | H | H | H | $-C(CH_3)_3$ | O | $-CH_2CF_3$ | $n_D^{21.0}$ 1.5305 |
| (48) | $CH_3$ | $CH_3$ | H | H | H | $-C(CH_3)_3$ | S | $-CH(CH_3)_2$ | $n_D^{25.0}$ 1.5285 |
| (49) | $CH_3$ | $CH_3$ | H | H | H | $-C(CH_3)_3$ | S | $-CH_2CH(CH_3)_2$ | $n_D^{21.0}$ 1.5290 |
| (50) | $CH_3$ | $CH_3$ | H | H | H | $-C(CH_3)_2OCH_3$ | O | $-C_6H_4F$ (4-F) | $n_D^{24.5}$ 1.5325 |
| (51) | $CH_3$ | $CH_3$ | H | H | H | $-C(CH_3)_2CH_2CH_3$ | O | $-CH_2CF_3$ | $n_D^{22.0}$ 1.4812 |

TABLE 2-continued

Compounds represented by the formula

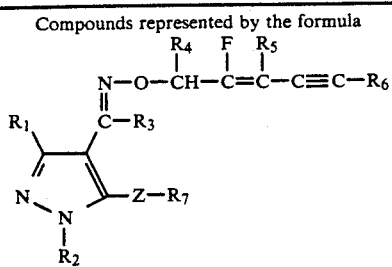

| Compound No. | $R_1$ | $R_2$ | $R_3$ | $R_4$ | $R_5$ | $R_6$ | Z | $R_7$ | Physical Properties |
|---|---|---|---|---|---|---|---|---|---|
| (52) | $CH_3$ | $CH_3$ | H | H | H | $H_3C\underset{\underset{Ph}{\|}}{\overset{CH_3}{\|}}Si-$ | O | phenyl | $n_D^{24.5}$ 1.5574 |
| (53) | $CH_3$ | $CH_3$ | H | H | H | $-C(CH_3)_3$ | O | $-CH_2C\equiv CC_2H_5$ | $n_D^{25.0}$ 1.5162 |
| (54) | $CH_3$ | $CH_3$ | H | H | H | $-C(CH_3)_3$ | O | $-CH(CH_2CH_3)_2$ | $n_D^{25.5}$ 1.5035 |
| (55) | $CH_3$ | $CH_3$ | H | H | H | $-C(CH_3)_3$ | O | $CH_3$ | $n_D^{24.0}$ 1.5120 |
| (56) | $CH_3$ | $CH_3$ | H | H | H | $-C(CH_3)_3$ | O | $-CH_2CF_2CF_3$ | $n_D^{23.0}$ 1.4561 |
| (57) | $-CH_2CH_3$ | $CH_3$ | H | H | H | $-C(CH_3)_3$ | O | $-CH(CH_3)_2$ | $n_D^{25.0}$ 1.5128 |
| (58) | $-CH_2CH_3$ | $CH_3$ | H | H | H | $-Si(CH_3)_3$ | O | 2,4-difluorophenyl | $n_D^{24.0}$ 1.5308 |
| (59) | $-CH_2CH_3$ | $CH_3$ | H | H | H | $-Si(CH_3)_3$ | O | phenyl | $n_D^{24.0}$ 1.5368 |
| (60) | $CH_3$ | $CH_3$ | H | H | H | $-Si(CH_3)_3$ | O | cyclopentyl | $n_D^{23.0}$ 1.5201 |
| (61) | $CH_3$ | $CH_3$ | H | H | H | $-Si(CH_3)_3$ | O | $-CH_2CH_2CF_3$ | $n_D^{23.5}$ 1.4685 |
| (62) | $CH_3$ | $CH_3$ | H | H | H | $-Si(CH_3)_3$ | O | $-CH_2CF_2CF_2CF_3$ | $n_D^{24.5}$ 1.4602 |

TABLE 2-continued
Compounds represented by the formula
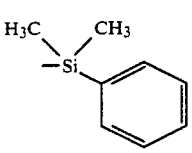
| Compound No. | R₁ | R₂ | R₃ | R₄ | R₅ | R₆ | Z | R₇ | Physical Properties |
|---|---|---|---|---|---|---|---|---|---|
| (63) | CH₃ | CH₃ | H | H | H | 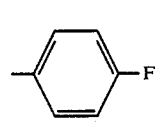 | O | 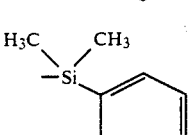 | $n_D^{25.0}$ 1.5476 |
| (64) | CH₃ | CH₃ | H | H | H | 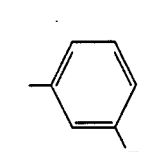 | O | 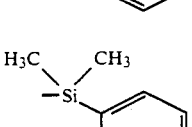 | $n_D^{23.5}$ 1.5457 |
| (65) | CH₃ | CH₃ | H | H | H | 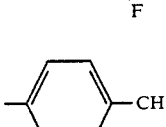 | O | 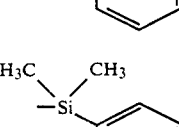 | $n_D^{25.0}$ 1.5569 |
| (66) | CH₃ | CH₃ | H | H | H | 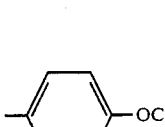 | O | 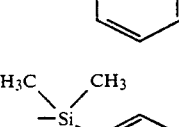 | $n_D^{24.5}$ 1.5548 |
| (67) | —CH₂CH₃ | CH₃ | H | H | H | 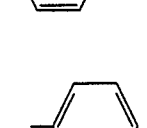 | O | 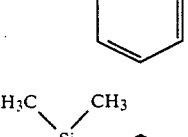 | $n_D^{23.0}$ 1.5561 |
| (68) | CH₃ | CH₃ | H | H | H | 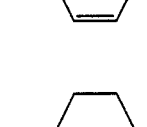 | O | 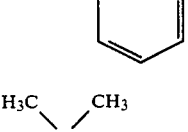 | $n_D^{24.5}$ 1.5285 |
| (69) | CH₃ | CH₃ | H | H | H | 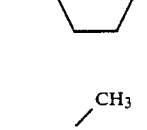 | O | —CH(CH₃)CH₃ | $n_D^{23.5}$ 1.5234 |
| (70) | CH₃ | CH₃ | H | H | H | 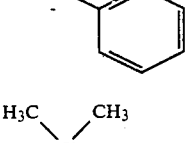 | O | —CH(CH₂CH₃)CH₃ | $n_D^{23.5}$ 1.5265 |
| (71) | CH₃ | CH₃ | H | H | H | 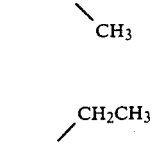 | O | —CH₂CF₃ | $n_D^{22.0}$ 1.5059 |

TABLE 2-continued

Compounds represented by the formula

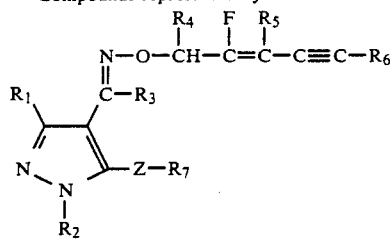

| Compound No. | $R_1$ | $R_2$ | $R_3$ | $R_4$ | $R_5$ | $R_6$ | Z | $R_7$ | Physical Properties |
|---|---|---|---|---|---|---|---|---|---|
| (72) | $CH_3$ | $CH_3$ | H | H | H | $H_3C$─Si($CH_3$)─Ph | O | ─$CH_2CF_2CF_3$ | $n_D^{25.0}$ 1.4985 |
| (73) | $CH_3$ | $CH_3$ | H | H | H | $H_3C$─Si($CH_3$)─Ph | O | ─$CH_2CF_2CF_2CF_3$ | $n_D^{24.0}$ 1.4913 |
| (74) | $CH_3$ | $CH_3$ | H | H | H | $H_3C$─Si($CH_3$)─Ph | O | ─CH($CH_3$)$CF_2CF_3$ | $n_D^{23.5}$ 1.4906 |
| (75) | $CH_3$ | $CH_3$ | H | H | H | ─C($CH_3$)$_2$OCH$_3$ | O | 3-F-C$_6$H$_4$─ | $n_D^{23.0}$ 1.5258 |
| (76) | $CH_3$ | $CH_3$ | H | H | H | ─C($CH_3$)$_2$OCH$_3$ | O | 4-CH$_3$-C$_6$H$_4$─ | $n_D^{25.0}$ 1.5326 |
| (77) | $CH_3$ | $CH_3$ | H | H | H | ─C($CH_3$)$_2$OCH$_3$ | O | 4-OCH$_3$-C$_6$H$_4$─ | $n_D^{24.5}$ 1.5318 |
| (78) | $CH_3$ | $CH_3$ | H | H | H | ─C($CH_3$)$_2$OCH$_3$ | O | 3,5-F$_2$-C$_6$H$_3$─ | $n_D^{23.0}$ 1.5251 |
| (79) | ─$CH_2CH_3$ | $CH_3$ | H | H | H | ─C($CH_3$)$_2$OCH$_3$ | O | C$_6$H$_5$─ | $n_D^{24.0}$ 1.5385 |
| (80) | $CH_3$ | $CH_3$ | H | H | H | ─C($CH_3$)$_2$OCH$_3$ | O | 4-Cl-C$_6$H$_4$─ | $n_D^{24.5}$ 1.5301 |

TABLE 2-continued

Compounds represented by the formula $$\underset{R_2}{\underset{|}{N}}\underset{N}{\overset{R_1}{\diagdown}}\hspace{-2pt}\underset{}{\overset{}{\diagup}}\hspace{-2pt}\underset{Z-R_7}{\overset{\underset{\parallel}{C-R_3}}{\overset{|}{\diagdown}}}\hspace{-2pt}\underset{}{\overset{N-O-CH-C=C-C\equiv C-R_6}{\overset{R_4 \quad F \quad R_5}{|\quad\;\;|\quad\;\;|}}}$$

| Compound No. | $R_1$ | $R_2$ | $R_3$ | $R_4$ | $R_5$ | $R_6$ | Z | $R_7$ | Physical Properties |
|---|---|---|---|---|---|---|---|---|---|
| (81) | $CH_3$ | $CH_3$ | H | H | H | $-C(CH_3)(CH_3)(OCH_3)$ | O | $-CH(CH_3)(CH_2CH_3)$ | $n_D^{25.0}$ 1.5083 |
| (82) | $CH_3$ | $CH_3$ | H | H | H | $-C(CH_3)(CH_3)(OCH_3)$ | O | $-CH(CH_3)(CH_2CH_2CH_3)$ | $n_D^{24.0}$ 1.5162 |
| (83) | $CH_3$ | $CH_3$ | H | H | H | $-C(CH_3)(CH_3)(OCH_3)$ | O | cyclopentyl | $n_D^{23.0}$ 1.5157 |
| (84) | $CH_3$ | $CH_3$ | H | H | H | $-C(CH_3)(CH_3)(OCH_3)$ | O | $-CH_2CF_3$ | $n_D^{23.0}$ 1.4808 |
| (85) | $CH_3$ | $CH_3$ | H | H | H | $-C(CH_3)(CH_3)(OCH_3)$ | O | $-CH_2CF_2CF_3$ | $n_D^{24.0}$ 1.4752 |
| (86) | $CH_3$ | $CH_3$ | H | H | H | $-C(CH_3)(CH_3)(OCH_3)$ | O | $-CH_2CF_2CF_2CF_3$ | $n_D^{24.5}$ 1.4649 |
| (87) | $CH_3$ | $CH_3$ | H | H | H | $-C(CH_3)_3$ | O | $-CH(CH_3)(CF_2CF_3)$ | $n_D^{23.0}$ 1.4763 |
| (88) | $CH_3$ | $CH_3$ | H | H | H | $-C(CH_3)_3$ | O | $-CH(CH_3)(CF_2CF_2CF_3)$ | $n_D^{25.0}$ 1.4511 |
| (89) | $CH_3$ | $CH_3$ | H | H | H | $-C(CH_3)_3$ | O | $-CH_2CF_2CF_2CF_2CF_2H$ | $n_D^{25.0}$ 1.4578 |
| (90) | $CH_3$ | $CH_3$ | H | H | H | $-C(CH_2CH_3)(CH_3)(CH_3)$ | O | phenyl | $n_D^{23.5}$ 1.5317 |
| (91) | $CH_3$ | $CH_3$ | H | H | H | $-C(CH_2CH_3)(CH_3)(CH_3)$ | O | 4-chlorophenyl | $n_D^{23.5}$ 1.5308 |

TABLE 2-continued

Compounds represented by the formula $$\begin{array}{c} R_4 \quad F \quad R_5 \\ N-O-CH=C=C-C\equiv C-R_6 \\ \| \\ C-R_3 \end{array}$$

(pyrazole ring with $R_1$, $R_2$, $Z-R_7$ substituents)

| Compound No. | $R_1$ | $R_2$ | $R_3$ | $R_4$ | $R_5$ | $R_6$ | Z | $R_7$ | Physical Properties |
|---|---|---|---|---|---|---|---|---|---|
| (92) | CH$_3$ | CH$_3$ | H | H | H | -C(CH$_2$CH$_3$)(CH$_3$)(CH$_3$) | O | 4-F-C$_6$H$_4$- | $n_D^{23.0}$ 1.5295 |
| (93) | CH$_3$ | CH$_3$ | H | H | H | -C(CH$_2$CH$_3$)(CH$_3$)(CH$_3$) | O | 3-F-C$_6$H$_4$- | $n_D^{24.5}$ 1.5316 |
| (94) | -CH$_2$CH$_3$ | CH$_3$ | H | H | H | -C(CH$_2$CH$_3$)(CH$_3$)(CH$_3$) | O | C$_6$H$_5$- | $n_D^{25.0}$ 1.5345 |
| (95) | -CH$_2$CH$_3$ | CH$_3$ | H | H | H | -C(CH$_2$CH$_3$)(CH$_3$)(CH$_3$) | O | 4-Cl-C$_6$H$_4$- | $n_D^{24.5}$ 1.5326 |
| (96) | CH$_3$ | CH$_3$ | H | H | H | -CH(CH$_3$)$_2$ | O | C$_6$H$_5$- | $n_D^{24.0}$ 1.5311 |
| (97) | CH$_3$ | CH$_3$ | H | H | H | -CH(CH$_3$)$_2$ | O | 4-Cl-C$_6$H$_4$- | $n_D^{23.5}$ 1.5314 |
| (98) | CH$_3$ | CH$_3$ | H | H | H | -CH(CH$_3$)$_2$ | O | 4-F-C$_6$H$_4$- | $n_D^{24.0}$ 1.5323 |
| (99) | CH$_3$ | CH$_3$ | H | H | H | -CH(CH$_3$)$_2$ | O | 3-F-C$_6$H$_4$- | $n_D^{24.0}$ 1.5318 |
| (100) | -CH$_2$CH$_3$ | CH$_3$ | H | H | H | -CH(CH$_3$)$_2$ | O | C$_6$H$_5$- | $n_D^{23.0}$ 1.5293 |
| (101) | -CH$_2$CH$_3$ | CH$_3$ | H | H | H | -CH(CH$_3$)$_2$ | O | 4-Cl-C$_6$H$_4$- | $n_D^{23.5}$ 1.5335 |

TABLE 2-continued

Compounds represented by the formula

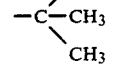

| Compound No. | R₁ | R₂ | R₃ | R₄ | R₅ | R₆ | Z | R₇ | Physical Properties |
|---|---|---|---|---|---|---|---|---|---|
| (102) | CH₃ | CH₃ | H | H | H | $-\underset{\underset{CH_3}{CH_3}}{\overset{CH_2CH_3}{C}}-$ | O | cyclohexyl-H | $n_D^{24.5}$ 1.5163 |
| (103) | CH₃ | CH₃ | H | H | H | $-\underset{\underset{CH_3}{CH_3}}{\overset{CH_2CH_3}{C}}-$ | O | cyclopentyl-H | $n_D^{25.0}$ 1.5172 |
| (104) | CH₃ | CH₃ | H | H | H | $-\underset{\underset{CH_3}{CH_3}}{\overset{CH_2CH_3}{C}}-$ | O | $-CH\underset{CH_2CH_3}{\overset{CH_3}{\big<}}$ | $n_D^{23.0}$ 1.5081 |
| (105) | CH₃ | CH₃ | H | H | H | $-\underset{\underset{CH_3}{CH_3}}{\overset{CH_2CH_3}{C}}-$ | O | —CH₂CF₂CF₃ | $n_D^{22.5}$ 1.4823 |
| (106) | CH₃ | CH₃ | H | H | H | $-\underset{\underset{CH_3}{CH_3}}{\overset{CH_2CH_3}{C}}-$ | O | $-CH\underset{CF_3}{\overset{CF_3}{\big<}}$ | $n_D^{23.5}$ 1.4786 |
| (107) | CH₃ | CH₃ | H | H | H | $-\underset{\underset{CH_3}{CH_3}}{\overset{CH_2CH_3}{C}}-$ | O | —CH₂CF₂CF₂CF₃ | $n_D^{23.5}$ 1.4762 |
| (108) | —CH₂CH₃ | CH₃ | H | H | H | $-\underset{\underset{CH_3}{CH_3}}{\overset{CH_2CH_3}{C}}-$ | O | cyclopentyl-H | $n_D^{23.5}$ 1.5166 |
| (109) | —CH₂CH₃ | CH₃ | H | H | H | $-\underset{\underset{CH_3}{CH_3}}{\overset{CH_2CH_3}{C}}-$ | O | —CH₂CF₂CF₃ | $n_D^{22.0}$ 1.4803 |
| (110) | CH₃ | CH₃ | H | H | H | $-CH\underset{CH_3}{\overset{CH_3}{\big<}}$ | O | cyclohexyl-H | $n_D^{24.5}$ 1.5125 |
| (111) | CH₃ | CH₃ | H | H | H | $-CH\underset{CH_3}{\overset{CH_3}{\big<}}$ | O | cyclopentyl-H | $n_D^{24.0}$ 1.5204 |
| (112) | CH₃ | CH₃ | H | H | H | $-CH\underset{CH_3}{\overset{CH_3}{\big<}}$ | O | $-CH\underset{CH_2CH_3}{\overset{CH_3}{\big<}}$ | $n_D^{25.5}$ 1.5089 |

TABLE 2-continued

Compounds represented by the formula $$\underset{R_2}{\underset{|}{N}}\text{-pyrazole with } C(=N-O-CH(R_4)-C(F)=C(R_5)-C\equiv C-R_6)-R_3 \text{ and } Z-R_7$$

| Compound No. | $R_1$ | $R_2$ | $R_3$ | $R_4$ | $R_5$ | $R_6$ | Z | $R_7$ | Physical Properties |
|---|---|---|---|---|---|---|---|---|---|
| (113) | $CH_3$ | $CH_3$ | H | H | H | $-CH(CH_3)_2$ | O | $-CH_2CF_3$ | $n_D^{23.5}$ 1.4872 |
| (114) | $CH_3$ | $CH_3$ | H | H | H | $-CH(CH_3)_2$ | O | $-CH_2CF_2CF_3$ | $n_D^{24.0}$ 1.4712 |
| (115) | $-CH_2CH_3$ | $CH_3$ | H | H | H | $-CH(CH_3)_2$ | O | cyclohexyl | $n_D^{24.0}$ 1.5159 |
| (116) | $-CH_2CH_3$ | $CH_3$ | H | H | H | $-CH(CH_3)_2$ | O | $-CH_2CF_2CF_3$ | $n_D^{24.5}$ 1.4805 |
| (117) | $CH_3$ | $CH_3$ | H | H | H | H | O | phenyl | $n_D^{25.5}$ 1.5492 |
| (118) | $CH_3$ | $CH_3$ | H | H | H | H | O | 4-Cl-phenyl | $n_D^{24.0}$ 1.5413 |
| (119) | $CH_3$ | $CH_3$ | H | H | H | $-C(CH_3)_3$ | O | 3-OCH$_3$-phenyl | $n_D^{22.0}$ 1.5365 |
| (120) | $CH_3$ | $CH_3$ | H | H | H | $-C(CH_3)=CH_2$ | O | phenyl | $n_D^{25.5}$ 1.5600 |
| (121) | $CH_3$ | $CH_3$ | H | H | H | $-C(CH_3)=CH_2$ | O | 4-CH$_3$-phenyl | $n_D^{25.5}$ 1.5621 |
| (122) | $CH_3$ | $CH_3$ | H | H | H | $-C(CH_3)=CH_2$ | O | 4-OCH$_3$-phenyl | $n_D^{25.0}$ 1.5485 |
| (123) | $CH_3$ | $CH_3$ | H | H | H | phenyl | O | phenyl | $n_D^{24.0}$ 1.6003 |

TABLE 2-continued

Compounds represented by the formula

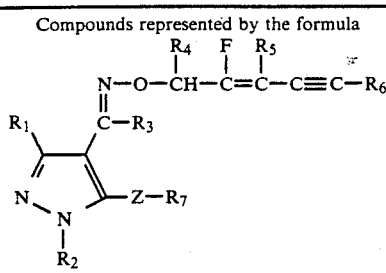

| Compound No. | $R_1$ | $R_2$ | $R_3$ | $R_4$ | $R_5$ | $R_6$ | Z | $R_7$ | Physical Properties |
|---|---|---|---|---|---|---|---|---|---|
| (124) | $CH_3$ | $CH_3$ | H | H | H | phenyl | O | 4-F-phenyl | $n_D^{24.0}$ 1.5997 |
| (125) | $CH_3$ | $CH_3$ | H | H | H | phenyl | O | 3-F-phenyl | $n_D^{22.5}$ 1.5973 |
| (126) | $CH_3$ | $CH_3$ | H | H | H | phenyl | O | 4-$OCH_3$-phenyl | $n_D^{22.5}$ 1.6012 |
| (127) | $CH_3$ | $CH_3$ | H | H | H | phenyl | O | cyclopentyl | $n_D^{23.0}$ 1.5790 |
| (128) | $CH_3$ | $CH_3$ | H | H | H | phenyl | O | $-CH_2CF_2CF_3$ | $n_D^{24}$ 1.5356 |
| (129) | $CH_3$ | $CH_3$ | H | H | H | cyclohexyl | O | $-CH(CH_2CH_3)CH_3$ | $n_D^{24.0}$ 1.5192 |
| (130) | $CH_3$ | $CH_3$ | H | H | H | cyclohexyl | O | $-CH_2CH_2CH_2CH_3$ | $n_D^{23.6}$ 1.5181 |
| (131) | $CH_3$ | $CH_3$ | H | H | H | cyclohexyl | O | $-CH_2CF_3$ | $n_D^{22.5}$ 1.4745 |
| (132) | $CH_3$ | $CH_3$ | H | H | H | cyclohexyl | O | $-CH(CH_3)_2$ | $n_D^{22.5}$ 1.5189 |
| (133) | $CH_3$ | $CH_3$ | H | H | H | cyclohexyl | O | $-CH_2CF_2CF_3$ | $n_D^{25.0}$ 1.4891 |

PRODUCTION EXAMPLE 8

(Production of the Intermediate)

Ten grams (0.122 mole) of 3,3-dimethyl-1-butyne was dissolved in 100 ml of anhydrous tetrahydrofuran, and the resulting solution was cooled to −40° C. or less in a dry ice-acetone bath. Under a stream of a nitrogen gas, 81.13 ml of a 1.5M hexane solution of n-butyllithium was added dropwise at −40° C. or less with stirring. After aging ageing the reaction solution at −50° C. for 30 minutes, 9.01 g (0.122 mole) of 2-fluoroacrolein was added dropwise at −50° C. or less. After the reaction mixture was allowed to stand overnight at room temperature, it was poured into 200 ml of ice water and extracted with two 100-ml portions of ethyl acetate. The organic layers were combined, washed once with 100 ml of a saturated aqueous sodium chloride solution and concentrated under reduced pressure. The resulting oily product was distilled under reduced pressure to obtain 11 g of 2-fluoro-3-hydroxy-6,6-dimethylhept-1-ene-4-yne (bp$_{20}$, 86° C.).

PRODUCTION EXAMPLE 9

(Production of the Intermediate)

Ten grams (0.102 mole) of 3,3-dimethyl-3-methoxy-1-propyne, produced according to the method described in Zh. Org. Khim., 2(11), 1969–1973 (1966), was dissolved in 100 ml of anhydrous tetrahydrofuran, and the resulting solution was cooled to −40° C. or less in a dry ice-acetone bath. Under a stream of a nitrogen gas, 68 ml of 1.5M hexane solution of n-butyllithium was added dropwise at −40° C. or less with stirring. After aging the reaction solution at −50° C. for 30 minutes, 7.53 g (0.102 mole) of 2-fluoroacrolein was added dropwise at −50° C. or less. After the reaction mixture was allowed to stand overnight at room temperature, it was poured into 200 ml of ice water and extracted with two 100-ml portions of ethyl acetate. The organic layers were combined, washed once with 100 ml of a saturated aqueous sodium chloride solution and concentrated under reduced pressure. The residue was distilled under reduced pressure to obtain 3 g of 2-fluoro-3-hydroxy-6,6-dimethyl-6-methoxyhex-1-ene-4-yne.

$n_D^{23.0}$ 1.4912.

Thus, compounds of the formula (XI) shown in Table 3 can be obtained in a similar manner.

TABLE 3

Compounds represented by the formula:

$$R_4-CH=C(F)-C(R_5)(OH)-C\equiv C-R_6'$$

| R$_4$ | R$_5$ | R$_6'$ | Physical properties |
|---|---|---|---|
| H | H | −C(CH$_2$CH$_3$)(CH$_3$)−CH$_3$ | $n_D^{25.0}$ 1.4516 |
| H | H | −CH(CH$_3$)−CH$_3$ | $n_D^{24.0}$ 1.4438 |

TABLE 3-continued

Compounds represented by the formula:

$$R_4-CH=C(F)-C(R_5)(OH)-C\equiv C-R_6'$$

| R$_4$ | R$_5$ | R$_6'$ | Physical properties |
|---|---|---|---|
| H | H | cyclohexyl (−C$_6$H$_{11}$) | $n_D^{23.5}$ 1.4751 |
| H | H | phenyl | bp$_{20}$ 144–146° C. |
| H | H | −C(CH$_3$)(CH$_3$)−OCH$_3$ | |
| H | H | −C(CH$_3$)=CH$_2$ | |

PRODUCTION EXAMPLE 10

(Production of the intermediate)

Ten grams (0.064 mole) of 2-fluoro-3-hydroxy-6,6-dimethylhept-1-ene-4-yne was added 200 ml of concentrated hydrochloric acid, and the mixture was aged for 5 hours at room temperature with stirring. The reaction mixture was extracted with three 100 ml portions of diethylether. The organic layers were combined, washed once with 100 ml of a saturated aqueous sodium chloride solution and concentrated under reduced pressure. The resulting oily product was distilled under reduced pressure to obtain 5 g of 1-chloro-2-fluoro-6,6-dimethylhept-2-ene-4-yne.

bp$_{18}$ 86°–88° C.

Thus, compounds of the formula (III) shown in Table 4 can be obtained in a similar manner.

TABLE 4

Compounds represented by the formula:

$$W_1-CH(R_4)-C(F)=C(R_5)-C\equiv C-R_6'$$

| R$_4$ | R$_5$ | R$_6'$ | W$_1$ | Physical properties |
|---|---|---|---|---|
| H | H | −C(CH$_3$)(CH$_3$)−CH$_3$ | Br | $n_D^{24.4}$ 1.4979 |
| H | H | −C(CH$_2$CH$_3$)(CH$_3$)−CH$_3$ | Cl | $n_D^{25.0}$ 1.4803 |
| H | H | −CH(CH$_3$)−CH$_3$ | Cl | $n_D^{24.0}$ 1.4786 |

TABLE 4-continued

Compounds represented by the formula:

$$W_1-CH-\underset{|}{C}=\underset{|}{C}-C\equiv C-R_6'$$
$$\phantom{W_1-CH}R_4\phantom{-}F\phantom{-}R_5$$

| $R_4$ | $R_5$ | $R_6'$ | $W_1$ | Physical properties |
|---|---|---|---|---|
| H | H | —⟨cyclohexyl-H⟩ | Cl | |
| H | H | —⟨phenyl⟩ | Cl | $n_D^{24.0}$ 1.5062 |
| H | H | —C(CH$_3$)=CH$_2$ | Cl | $n_D^{23.0}$ 1.4717 |

PRODUCTION EXAMPLE 11

(Production of the intermediate)

Ten grams (0.064 mole) of 2-fluoro-3-hydroxy-6,6-dimethylhept-1-ene-4-yne was dissolved in 100 ml of hexane, and to 50 mg ($6.8 \times 10^{-4}$ mole) of N,N-dimethylformamide and 11.42 g (0.095 mole) of thionyl chloride were added to the resulting solution. The mixture was reacted overnight at room temperature with stirring with a hydrogen chloride gas trap mounted on the reactor. The reaction mixture was concentrated under reduced pressure. The resulting oily product was distilled under reduced pressure to obtain 10.1 g of 2-fluoro-3-chloro-6,6-dimethylhept-1-ene-4-yne.

bp$_{40}$ 78°–82° C.

Thus, compounds of the formula (VI) shown in Table 5 can be obtained in a similar manner.

TABLE 5

Compounds represented by the formula:

$$R_4-CH=\underset{|}{C}-\underset{|}{C}-C\equiv C-R_6'$$
$$\phantom{R_4-CH=}F\phantom{-}R_5$$
$$\phantom{R_4-CH=C-}W_2$$

| $R_4$ | $R_5$ | $R_6'$ | $W_2$ | Physical properties |
|---|---|---|---|---|
| H | H | —C(CH$_3$)$_2$CH$_2$CH$_3$ | Cl | $n_D^{24.0}$ 1.4759 |
| H | H | —CH(CH$_3$)$_2$ | Cl | $n_D^{25.0}$ 1.4811 |
| H | H | —⟨cyclohexyl-H⟩ | Cl | |

TABLE 5-continued

Compounds represented by the formula:

$$R_4-CH=\underset{|}{C}-\underset{|}{C}-C\equiv C-R_6'$$
$$\phantom{R_4-CH=}F\phantom{-}R_5$$
$$\phantom{R_4-CH=C-}W_2$$

| $R_4$ | $R_5$ | $R_6'$ | $W_2$ | Physical properties |
|---|---|---|---|---|
| H | H | —⟨phenyl⟩ | Cl | |
| H | H | —C(CH$_3$)$_2$OCH$_3$ | Cl | $n_D^{24.5}$ 1.4810 |
| H | H | —C(CH$_3$)=CH$_2$ | Cl | $n_D^{23.5}$ 1.4734 |

PRODUCTION EXAMPLE 12

(Production of the intermediate)

1.87 grams (0.0115 mole) of N-hydroxyphthalimide was dissolved in 20 ml of N,N-dimethylformamide, and 2 g (0.0115 mole) of 1-chloro-2-fluoro-6,6-dimethylhept-2-ene-4-yne and 1.27 g (0.0127 mole) of triethylamine were added to the resulting solution. The mixture was reacted at 60° C. for 5 hours with stirring. The reaction mixture was then poured into 200 ml of ice water and extracted with two 100-ml portions of ethyl acetate. The organic layers were combined, washed once with 100 ml of a saturated aqueous sodium chloride solution and concentrated under reduced pressure. The residue was subjected to column chromatography on silica gel to obtain 0.7 g of hydroxyphthalimide O-2-fluoro-6,6-dimethylhept-2-ene-4-ynyl ether.

0.5 gram ($1.7 \times 10^{-3}$ mole) of N-hydroxyphthalimide O-2-fluoro-6,6-dimethylhept-2-ene-4-ynyl ether was dissolved in 10 ml of toluene, and 0.24 g ($3.4 \times 10^{-3}$ mole) of hydroxylamine hydrochloride, 10 ml of water and 28 mg ($8.5 \times 10^5$ mole) of tetra-n-butylammonium bromide was added to the resulting mixture. The reaction mixture was violently stirred, and 4.1 ml of a 0.5% aqueous sodium hydroxide solution was added dropwise at room temperature. After aging the solution at room temperature for 10 hours with stirring, the solution was separated into two layers. The aqueous layer was extracted once with 50 ml of toluene. The organic layers were combined and washed with 50 ml of a saturated aqueous sodium chloride solution. The organic layer was concentrated under reduced pressure to obtain 0.1 g of hydroxylamine O-2-fluoro-6,6-dimethylhept-2-ene-4-ynyl ether.

$n_D^{24}$ 1.5116.

Thus, compounds of the formula (V) shown in Table 6 can be obtained in a similar manner.

TABLE 6

Compounds represented by the formula:

$$H_2N-O-\underset{R_4}{\underset{|}{CH}}-\underset{F}{\underset{|}{C}}=\underset{R_5}{\underset{|}{C}}-C\equiv C-R_6'$$

| R$_4$ | R$_5$ | R$_6'$ | Physical properties |
|---|---|---|---|
| H | H | −C(CH$_2$CH$_3$)(CH$_3$)(CH$_3$) | $n_D^{24.5}$ 1.4911 |
| H | H | −CH(CH$_3$)(CH$_3$) | $n_D^{23.5}$ 1.4832 |
| H | H | cyclohexyl (−C$_6$H$_{11}$) | $n_D^{23.0}$ 1.5193 |
| H | H | phenyl | |
| H | H | −C(CH$_3$)(CH$_3$)(OCH$_3$) | |
| H | H | −C(CH$_3$)=CH$_2$ | $n_D^{25.0}$ 1.4863 |

The formulation examples will be shown below.

FORMULATION EXAMPLE 1

(Emulsifiable concentrate)

Ten parts of each of the compounds (1) to (133) are dissolved in a mixture of 35 parts of xylene and 35 parts of dimethylformamide, and 14 parts of polyoxyethylene styrylphenyl ether and 6 parts of calcium dodecylbenzenesulfonate are added to the resulting solution. The resulting mixture is well mixed with stirring to obtain a 10% emulsifiable concentrate of each compound.

FORMULATION EXAMPLE 2

(Wettable powder)

Twenty parts of each of the compounds (1) to (133) are added to a mixture of 4 parts of sodium lauryl sulfate, 2 parts of calcium lignosulfonate, 20 parts of synthetic hydrated silicon dioxide fine powders and 54 parts of diatomaceous earth. The resulting mixture is well mixed with stirring by a juice mixer to obtain a 20% wettable powder of each compound.

FORMULATION EXAMPLE 3

(Granule)

To 5 parts of each of the compounds (1), (2), (8), (9), (11), (12) and (17) are added 5 parts of synthetic hydrated silicon dioxide fine powders, 5 parts of sodium dodecylbenzenesulfonate, 30 parts of bentonite and 55 parts of clay, and the resulting mixture is well mixed with stirring. Thereafter, a suitable amount of water is added, and the mixture is further stirred, granulated on a granulator and air-dried to obtain a 5% granule of each compound.

FORMULATION EXAMPLE 4

(Dust)

One part of each of the compounds (1) to (133) is dissolved in a suitable amount of acetone, and 5 parts of synthetic hydrated silicon dioxide fine powders, 0.3 part of PAP and 93.7 parts of clay are added to resulting mixture. The mixture is well mixed with stirring on a juice mixer, and acetone is removed by vaporization to obtain a 1% dust of each compound.

FORMUATION EXAMPLE 5

(Flowable concentrate)

Twenty parts of each of the compounds (1), (2), (8), (9), (11), (12) and (17) and 1.5 parts of sorbitan trioleate are mixed with 28.5 parts of an aqueous solution containing 2 parts of polyvinyl alcohol. The resulting mixture is finely pulverized on a sand grinder to a particle size of 3μ or less. 40 parts of an aqueous solution containing 0.05 part of xanthane gum and 0.1 part of aluminum magnesium silicate and then 10 parts of propylene glycol are added to the resulting mixture. The mixture is then well mixed with stirring to obtain a 20% flowable concentrate of each compound.

FORMULATION EXAMPLE 6

(Oil spray)

0.1 part of the compound (5) is dissolved in a mixture of 5 parts of xylene and 5 parts of trichloroethane, and the resulting solution is mixed with 89.9 parts of deodorized kerosene to obtain a 0.1% oil spray.

Test examples will be shown below. In the examples, the present compounds used for test are shown by Compound Nos. in Table 2, and compounds used as controls a control are shown by Compound symbols in Table 7.

TABLE 7

| Compound symbol | Structural formula | Remarks |
|---|---|---|
| (A) | 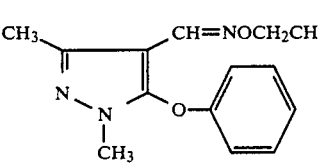 | Compound No. 800 described in EP No. 234,045-A2 234045A2. |

TABLE 7-continued

| Compound symbol | Structural formula | Remarks |
|---|---|---|
| (B) | $\begin{array}{c}CH_3O\phantom{xx}S\\ \phantom{xxx}\diagdown\|\phantom{xx}\\ \phantom{xxxxx}P-S-CH-COOC_2H_5\\ \phantom{xxx}\diagup\phantom{xxxxx}\|\\ CH_3O\phantom{xxxxx}CH_2-COOC_2H_5\end{array}$ | Malathion |
| (C) | $\begin{array}{c}H_3C\\ \phantom{x}\\ O\phantom{xxx}N-C_{13}H_{27}\\ \phantom{x}\\ H_3C\end{array}$ | Tridemorph |

TEST EXAMPLE 1

Insecticidal test on pesticide-resistant green rice leafhopper (*Nephotettix cincticeps*)

Each test compound was formulated into an emulsifiable concentrate according to Formulation example 1, and rice stems (length, about 12 cm) were dipped for 1 minute in the 200-fold aqueous dilute solution (500 ppm) of the emulsifiable concentrate. After air-drying, the rice stems were put in a test tube, and 10 adults of resistant green rice leafhoppers were released in the test tube. After one day, the number of dead and alive adults were established to obtain a morality. This test was repeated twice.

The results are shown in Table 8.

TABLE 8

| Test compound | Mortality (%) |
|---|---|
| (2) | 100 |
| (26) | 100 |
| (34) | 100 |
| (41) | 100 |
| (42) | 100 |
| (43) | 100 |
| (50) | 100 |
| (54) | 100 |
| (119) | 100 |
| (A) | 0 |
| (B) | 50 |
| No treatment | 0 |

TEST EXAMPLE 2

Insecticidal test on German cockroach (*Blattella germanica*)

On the bottom of a polyethylene cup of 5.5 cm in diameter was placed a filter paper of the same size, and 0.7 ml of the 200-fold aqueous dilute solution (500 ppm) of the emulsifiable concentrate, prepared from each test compound according to Formulation example 1, was dropped down to the filter paper. About 30 mg of sucrose was put in the cup as a bait, and two male adult of German cockroach were released in the cup. Six days after covering the cup, the number of dead and alive adults were established to obtain a mortality.

The results are shown in Table 9.

TABLE 9

| Test compound | Mortality (%) |
|---|---|
| (1) | 100 |
| (2) | 100 |
| (3) | 100 |
| (5) | 100 |

TABLE 9-continued

| Test compound | Mortality (%) |
|---|---|
| (6) | 100 |
| (17) | 100 |
| (34) | 100 |
| (35) | 100 |
| (36) | 100 |
| (41) | 100 |
| (54) | 100 |
| (56) | 100 |
| (A) | 0 |
| No treatment | 0 |

TEST EXAMPLE 3

Insecticidal test on tobacco cutworm (*Spodoptera litura*)

Each test compound was formulated into an emulsifiable concentrate according to Formulation example 1, and 2 ml of the 200-fold aqueous dilute solution (500 ppm) of the emulsifiable concentrate was impregnated into 13 g of artificial feeds for tabacco cutworm previously prepared in a polyethylene cup of 11 cm in diameter. Ten fourth instar larvae of tabacco cutworm were released in the cup. After six days, the number of dead and alive larvae were established to obtain a mortality. This test was repeated twice. At the same time, the degree of attack upon the artificial feeds was also examined. The degree of attack was judged based on the following standard:

—: Little attack is observed.
+: Attack is observed.
++: Attack is heavy, few artificial feeds being left.

The results are shown in Table 10.

TABLE 10

| Test Compound | Mortality (%) | Degree of attack |
|---|---|---|
| (1) | 100 | — |
| (2) | 100 | — |
| (3) | 100 | — |
| (4) | 100 | — |
| (5) | 100 | — |
| (6) | 100 | — |
| (7) | 100 | — |
| (8) | 100 | — |
| (14) | 100 | — |
| (15) | 100 | — |
| (16) | 100 | — |
| (17) | 100 | — |
| (19) | 100 | — |
| (20) | 100 | — |
| (21) | 100 | — |
| (23) | 100 | — |
| (25) | 100 | — |
| (26) | 100 | — |
| (28) | 100 | — |

TABLE 10-continued

| Test Compound | Mortality (%) | Degree of attack |
|---|---|---|
| (29) | 100 | — |
| (30) | 100 | — |
| (31) | 100 | — |
| (32) | 100 | — |
| (34) | 100 | — |
| (35) | 100 | — |
| (36) | 100 | — |
| (37) | 100 | — |
| (38) | 100 | — |
| (39) | 100 | — |
| (40) | 100 | — |
| (41) | 100 | — |
| (42) | 100 | — |
| (43) | 100 | — |
| (45) | 100 | — |
| (47) | 100 | — |
| (49) | 100 | — |
| (50) | 100 | — |
| (52) | 100 | — |
| (54) | 100 | — |
| (56) | 100 | — |
| (57) | 100 | — |
| (119) | 100 | — |
| (122) | 100 | — |
| (A) | 30 | ++ |
| No treatment | 0 | ++ |

TEST EXAMPLE 4

Insecticidal test on common mosquito (*Culex pipens pallens*)

The emulsifiable concentrate of each test compound prepared according to Formulation example 1 was diluted 200 times with water, and 0.7 ml of the dilute solution was added to 100 ml of ion-exchanged water (active ingredient concentration, 3.5 ppm). Twenty last instar larvae of common mosquito were released in the water, and after one day, the mortality was examined.

The standard for judging the effect was as follows:

Mortality (%)

a: Not less than 90%
b: Not less than 10% to less than 90%
c: Less than 10%

The results are shown in Table 11.

TABLE 11

| Test compound | Mortality (%) |
|---|---|
| (1) | a |
| (2) | a |
| (4) | a |
| (5) | a |
| (6) | a |
| (7) | a |
| (8) | a |
| (14) | a |
| (15) | a |
| (16) | a |
| (17) | a |
| (19) | a |
| (20) | a |
| (21) | a |
| (23) | a |
| (24) | a |
| (25) | a |
| (26) | a |
| (28) | a |
| (29) | a |
| (30) | a |
| (31) | a |
| (32) | a |
| (34) | a |
| (35) | a |
| (36) | a |
| (37) | a |
| (38) | a |
| (39) | a |
| (40) | a |
| (41) | a |
| (42) | a |
| (43) | a |
| (44) | a |
| (45) | a |
| (46) | a |
| (47) | a |
| (48) | a |
| (49) | a |
| (50) | a |
| (52) | a |
| (54) | a |
| (56) | a |
| (57) | a |
| (119) | a |
| (120) | a |
| (121) | a |
| (122) | a |
| (A) | c |
| No treatment | c |

TEST EXAMPLE 5

Acaricidal test on carmine spider mite (*Tetranychus cinnabarius*)

Female adult carmine spider mites mite were parasitized, at a rate of 10 adults/leaf, on potted kidney bean (in the primary leaf stage) 7 days after seeding, and placed in a constant-temperature room kept at 25° C. After 6 days, the emulsifiable concentrate of each test compound prepared according to Formulation example 1 was diluted with water to an active ingredient concentration of 500 ppm, and the dilute solution was sprayed onto the plant at a rate of 15 ml/pot on a turn table. At the same time, the soil was drenched with 2 ml of the same dilute solution. After 8 days, the degree of damage to each plant by the mite was examined. The standard for judging the effect was as follows:

—: Little damage is observed.
+: Slight damage is observed.
++: Same damage as in the untreated plot is observed.

The results are shown in Table 12.

TABLE 12

| Test compound | Effect |
|---|---|
| (1) | — |
| (2) | — |
| (3) | — |
| (4) | — |
| (5) | — |
| (6) | — |
| (7) | — |
| (8) | — |
| (9) | — |
| (10) | + |
| (11) | — |
| (12) | + |
| (13) | — |
| (14) | — |
| (15) | — |
| (16) | — |
| (17) | — |
| (18) | — |
| (19) | + |
| (20) | — |
| (21) | — |
| (22) | + |
| (23) | — |

TABLE 12-continued

| Test compound | Effect |
| --- | --- |
| (24) | − |
| (25) | + |
| (26) | − |
| (27) | − |
| (28) | − |
| (29) | − |
| (30) | − |
| (31) | − |
| (32) | − |
| (33) | − |
| (34) | − |
| (35) | − |
| (36) | − |
| (37) | − |
| (38) | − |
| (39) | − |
| (40) | − |
| (41) | − |
| (42) | − |
| (43) | − |
| (44) | − |
| (45) | − |
| (46) | + |
| (47) | + |
| (48) | + |
| (49) | − |
| (50) | − |
| (51) | + |
| (52) | − |
| (53) | + |
| (54) | + |
| (55) | + |
| (56) | − |
| (57) | − |
| (119) | + |
| (120) | + |
| (121) | + |
| (122) | + |
| No treatment | ++ |

TEST EXAMPLE 6

Controlling test on blast of rice (*Pyricularia oryzae*) (preventive effect)

Plastic pots were filled with sandy loam, and rice (var., Kinki No. 33) was sowed and cultivated for 20 days in a greenhouse to obtain rice seedlings. The emulsifiable concentrates of the test compounds obtained according to Formulation example 1 were each diluted with water to a prescribed concentration and foliar-applied onto the seedlings so that the spray liquor thoroughly adhered to the leaf surface. After the spraying, the seedlings were air-dried and inoculated by spraying a spore suspension of *Pyricularia oryzae*. After the inoculation, the seedlings were kept at 28° C. for 4 days at 28° C. under dark and very humid conditions, and then the controlling activity was examined.

The controlling activity was evaluated in the six stages described below, 5, 4, 3, 2, 1 and 0, by macroscopically observing the condition of the disease of the test plants, i.e. the degrees of colony and infected area on the leaves, stems, etc., at the time of examination.

5: Colony or infected area is not observed at all.
4: About 10% of colony or infected area is observed.
3: About 30% of colony or infected area is observed.
2: About 50% of colony or infected area is observed.
1: About 70% of colony or infected area is observed.
0: More than about 70% of colony or infected area is observed, there being no difference in the condition of disease between the treated and untreated plots.

The results are shown in Table 13.

TABLE 13

| Test Compound | Concentration (ppm) | Controlling activity |
| --- | --- | --- |
| (1) | 200 | 5 |
| (2) | 200 | 5 |
| (15) | 200 | 4 |
| (16) | 200 | 3 |
| (17) | 200 | 5 |
| (C) | 200 | 0 |

TEST EXAMPLE 7

Controlling test on sheath blight of rice (*Rhizoctonia solani*) (preventive effect)

Plastic pots were filled with sandy loam, and rice (var., Kinki No. 33) was sowed and cultivated for 28 days in a greenhouse to obtain rice seedlings. The emulsifiable concentrates of the test compounds obtained according to Formulation example 1 were each diluted with water to a prescribed concentration and foliar-applied onto the seedlings so that the spray liquor thoroughly adhered to the leaf surface. After the spraying, the seedlings were air-dried and inoculated by spraying a disc-inocular suspension of *Rhizoctonia solani*. After the inoculation, the sedlings were kept for 4 days under dark and very humid conditions and then the controlling activity was examined based on the same evaluation standard as in Test example 6.

The results are shown in Table 14.

TABLE 14

| Test Compound | Concentration (ppm) | Controlling activity |
| --- | --- | --- |
| (1) | 200 | 4 |
| (24) | 200 | 3 |
| (25) | 200 | 4 |
| (C) | 200 | 0 |

TEST EXAMPLE 8

Controlling test on powdery mildew of wheat (*Erysiphe graminis* f. sp. tritici)(curative effect)

Plastic pots were filled with sandy loam, and wheat (var., Norin No. 73) was sowed and cultivated for 10 days in a greenhouse to obtain wheat seedlings in the second 2nd leaf stage. The seedlings were inoculated by sprinkling with spores of *Erysiphe graminis* f. sp. tritici. After the inoculation, the seedlings were cultivated for 3 days in a greenhouse at 23° C. Thereafter, emulsifiable concentrates of the test compounds obtained according to Formulation example 1 were each diluted with water to a prescribed concentration and foliar-applied onto the seedlings so that the spray liquor thoroughly adhered to the leaf surface. After the spraying, the seedlings were cultivated for 6 days in a greenhouse at 23° C., and the controlling activity was examined based on the same evaluation standard as in Test example 6.

The results are shown in Table 15.

TABLE 15

| Test Compound | Concentration (ppm) | Controlling activity |
| --- | --- | --- |
| (1) | 50 | 5 |
| | 12.5 | 5 |
| (2) | 50 | 5 |
| | 12.5 | 5 |
| (C) | 50 | 3 |

TABLE 15-continued

| Test Compound | Concentration (ppm) | Controlling activity |
| --- | --- | --- |
| | 12.5 | 0 |

TEST EXAMPLE 9

Controlling test on leaf rust of wheat. (*Puccinia recondita*) (curative effect)

Plastic pots were filled with sandy loam, and wheat (var., Norin No. 73) was sowed and cultivated for 10 days in a greenhouse to obtain wheat seedlings in the second leaf stage. The seedlings were inoculated with spores of *Puccinia recondita*.

After the inoculation, the seedlings were cultivated for 1 day at 23° C. under very humid conditions. Thereafter, the emulsifiable concentrates of the test compounds obtained according to Formulation example 1 were each diluted with water to a prescribed concentration and foliar-applied onto the seedlings so that the spray liquor thoroughly adhered to the leaf surface. After the spraying, the seedlings were cultivated for 6 days at 23° C. in light, and the controlling activity was examined based on the same evaluation standard as in Test example 6.

The results are shown in Table 16.

TABLE 16

| Test Compound | Concentration (ppm) | Controlling activity |
| --- | --- | --- |
| (1) | 200 | 5 |
| | 50 | 5 |
| | 12.5 | 5 |
| (2) | 200 | 5 |
| | 50 | 5 |
| | 12.5 | 5 |
| (5) | 200 | 5 |
| (15) | 200 | 5 |
| (16) | 200 | 5 |
| (17) | 200 | 5 |
| (21) | 200 | 3 |
| (25) | 200 | 3 |
| (26) | 200 | 5 |
| (C) | 200 | 0 |

TEST EXAMPLE 10

Controlling test on speckled leaf blotch of wheat (Septoria tritici) (curative effect)

Plastic pots were filled with sandy loam, and wheat (var., Norin No. 73) was sowed and cultivated for 8 days in a greenhouse to obtain wheat seedlings. The seedlings were inoculated by spraying with a spore suspension of *Septoria tritici*. After the inoculation, the seedlings were kept at 15° C. for 3 days under dark and very humid conditions and then cultivated for 4 days under lighting. Thereafter, the flowable concentrates of the test compounds obtained according to Formulation example 5 were each diluted with water to a prescribed concentration and foliar-applied onto the seedlings so that the spray liquor thoroughly adhered to the leaf surface. After the spraying, the seedlings were cultivated for 11 days at 15° C. under lighting, and the controlling activity was examined based on the same evaluation standard as in Test example 6.

The results are shown in Table 17.

TABLE 17

| Test Compound | Concentration (ppm) | Controlling activity |
| --- | --- | --- |
| (1) | 200 | 4 |
| (2) | 200 | 4 |
| (17) | 200 | 3 |
| (21) | 200 | 3 |
| (C) | 200 | 0 |

TEST EXAMPLE 11

Controlling test on late blight of tomato (*Phytophthora infestans*) (preventive effect)

Plastic pots were filled with sandy loam, and tomato (var., Ponteroza) was sowed and cultivated for 20 days in a greenhouse to obtain tomato seedlings. The wettable powders of the test compounds obtained according to Formulation example 2 were each diluted with water to a prescribed concentration and foliar-applied onto the seedlings so that the spray liquor thoroughly adhered to the leaf surface. After the spraying, the seedlings were inoculated by spraying the spore suspension of *Phytophthora infestans*. After the inoculation, the seedlings were kept at 20° C. for 1 day under very humid conditions and then cultivated for 5 days in light. The controlling activity was then examined based on the same evalutation standard as in Test example 6.

The results are shown in Table 18.

TABLE 18

| Test Compound | Concentration (ppm) | Controlling activity |
| --- | --- | --- |
| (1) | 200 | 4 |
| | 50 | 4 |
| | 12.5 | 3 |
| (2) | 200 | 5 |
| (16) | 200 | 4 |
| (17) | 200 | 4 |
| (C) | 200 | 0 |

TEST EXAMPLE 12

Controlling test on alternaria spot of Japanes radish (*Alternaria brassicicola*) (preventive effect)

Plastic pots were filled with sandy loam, and Japanese radish (var., Wase-40 nichi) was sowed and cultivated for 5 days in a greenhouse to obtain Japanese radish seedlings. The wettable powders of the test compounds obtained according to Formulation example 2 were each diluted with water to a prescribed concentration and foliar-applied onto the seedlings so that the spray liquor thoroughly adhered to the leaf surface. After the spraying, the seedlings were inoculated by spraying with a spore suspension of *Alternaria brassicicola*. After the inoculation, the seedlings were kept at 23° C. for 1 day under very humid conditions and then cultivated for 3 days in a greenhouse. The controlling activity was then examined based on the same evaluation standard as in Test example 6.

The results are shown in Table 19.

TABLE 19

| Test Compound | Concentration (ppm) | Controlling activity |
| --- | --- | --- |
| (1) | 200 | 5 |
| | 50 | 4 |
| | 12.5 | 3 |
| (2) | 200 | 5 |
| | 50 | 5 |

TABLE 19-continued

| Test Compound | Concentration (ppm) | Controlling activity |
|---|---|---|
| | 12.5 | 4 |
| (C) | 200 | 0 |

TEST EXAMPLE 13

Controlling test on downy mildew of cucumber (*Pseudoperonospora cubensis*) (curative effect)

Plastic pots were filled with sandy loam, and cucumber (var., Sagamihanjiro) was sowed and cultivated for 14 days in a greenhouse to obtain cucumber seedlings in the cotyledonous stage.

The seedlings were inoculated by spraying with a spore suspension of *Pseudoperonospora cubensis*. After the inoculation, the seedlings were kept at 20° C. for 1 day under very humid conditions. Thereafter, the wettable powders of the test compounds obtained according to Formulation example 1 were each diluted with water to a prescribed concentration and foliar-applied onto the seedlings so that the spray liquor thoroughly adhered to the leaf surface. After the spraying, the seedlings were cultivated for 8 days in light, and then the controlling activity was examined based on the same evaluation standard as in Test example 6.

Test results are shown in Table 20.

TABLE 20

| Test Compound | Concentration (ppm) | Controlling activity |
|---|---|---|
| (1) | 200 | 5 |
| (2) | 200 | 5 |
| (5) | 200 | 3 |
| (21) | 200 | 3 |
| (26) | 200 | 5 |
| (C) | 200 | 0 |

What is claimed is:

1. A compound represented by the formula,

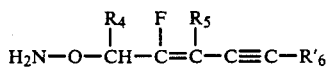

wherein each of $R_4$ and $R_5$, which may be the same or different, is a hydrogen atom or an alkyl group; and $R'_6$ is a hydrogen atom, or an alkyl, haloalkyl, alkenyl, alkoxyalkyl or alkylthioalkyl group, or an optionally substituted cycloalkyl, cycloalkenyl, phenyl or pyridyl group.

* * * * *